US006733450B1

(12) United States Patent
Alexandrov et al.

(10) Patent No.: US 6,733,450 B1
(45) Date of Patent: May 11, 2004

(54) THERAPEUTIC METHODS AND APPARATUS FOR USE OF SONICATION TO ENHANCE PERFUSION OF TISSUE

(75) Inventors: Andrei V. Alexandrov, Houston, TX (US); Jaroslaw A. Aronowski, Houston, TX (US); Anne W. Wojner, The Woodlands, TX (US)

(73) Assignee: Texas Systems, Board of Regents, Austin, TX (US)

( * ) Notice: Subject to any disclaimer, the term of this patent is extended or adjusted under 35 U.S.C. 154(b) by 486 days.

(21) Appl. No.: 09/627,077

(22) Filed: Jul. 27, 2000

(51) Int. Cl.[7] .................................................. A61B 8/00
(52) U.S. Cl. .............................. 600/439; 601/2; 601/3; 601/4; 604/22
(58) Field of Search ...................... 601/2, 3, 4; 600/439; 604/22

(56) References Cited

U.S. PATENT DOCUMENTS

| | | | |
|---|---|---|---|
| 3,951,140 A | 4/1976 | Eggleton et al. ............... 128/24 |
| 3,990,300 A | 11/1976 | Kossoff | |
| 4,526,168 A | 7/1985 | Hassler et al. | |
| 4,957,099 A | 9/1990 | Hassler | |
| 5,413,550 A | 5/1995 | Castel ........................... 601/2 |
| 5,501,655 A * | 3/1996 | Rolt et al. ...................... 601/3 |
| 5,620,409 A | 4/1997 | Venuto et al. .................. 601/2 |
| 5,620,479 A * | 4/1997 | Diederich ....................... 601/3 |
| 5,630,837 A * | 5/1997 | Crowley ........................ 601/2 |
| 5,664,570 A | 9/1997 | Bishop | |
| 5,752,515 A | 5/1998 | Jolesz et al. ............. 128/653.1 |
| 5,904,659 A | 5/1999 | Duarte et al. | |
| 6,086,535 A | 7/2000 | Ishibashi et al. | |
| 6,126,619 A * | 10/2000 | Peterson et al. ............... 601/2 |
| 6,267,734 B1 * | 7/2001 | Ishibashi et al. ............... 601/2 |
| 6,394,955 B1 * | 5/2002 | Perlitz ........................ 600/439 |

FOREIGN PATENT DOCUMENTS

| | | |
|---|---|---|
| DE | 41 20 593 C1 | 9/1992 |
| EP | 0 938 913 A2 | 1/1999 |

OTHER PUBLICATIONS

The National Institutes of Neurological Disorders and Stroke rt–PA Stroke Study Group. Tissue plasminogen activator for acute ischemic stroke. *N. Engl J Med.* 1995; 333:1581–1587.

del Zoppo GJ, Poeck K, Pessin MS, Wolpert SM, Furlan AJ, Ferbert A, Alberts MJ, Zivin JA, Wechsler L, Busse O, Greenlee, R, Brass L, Mohr JP, Feldmann E, Hacke W, Kase CS, Biller J, Green D, Otis SM. Recombinant tissue plasminogen activator in acute thrombotic and embolic stroke. *Ann Neurol.* 1992; 32:78–86.

(List continued on next page.)

*Primary Examiner*—Marvin M. Lateef
*Assistant Examiner*—Devaang Shah
(74) *Attorney, Agent, or Firm*—Sue Z. Shaper

(57) ABSTRACT

Ultrasound methods and apparatus for reducing tissue damage from ischemia by means of insonation through intact skin and/or bone, the insonation preferably promoting thrombolysis, reducing edema and promoting microcirculation, recanalization, increased collateraled interstitial flow and delivery of lytic agents to clots located in supplying arteries as well as nutrients or therapeutic agent to the ischemic tissue. A portion of an organ affected by ischemia or the entire organ is exposed to low frequency low power ultrasound generated by multiple transducers of variable power limits which at least partially surround an organ, preferably at least 90% of a skull surface, for instance. Studies indicate the approach maintains biological tissue function or viability in the setting of reduced perfusion by exposing the tissue or organ to ultrasound energy transmission.

52 Claims, 15 Drawing Sheets

OTHER PUBLICATIONS

Akiyama M, Ishibashi T, Yamada T, Furuhata H. Low-frequency ultrasound penetrates the cranium, and enhances thrombolysis in vitro. Abstract of *Neurosurgery 1998;* 43:828–832.

Behrens S, Daffertshofer M, Spiegel D, Hennerici M. Low-frequency, low intensity ultrasound accelerates thrombolysis through the skull. Abstract of *Ultrasound Med Biol 1999;* 25:269–273.

Braaten JV, Goss RA, Francis CW. Ultrasound reversibility disaggregates fibrin fibers. Abstract of *Thromb Haemost 1997;* 78:1063–1068.

Kondo I, Mizuhige K, Ueda T, Masugata H, Ohmori K, Matsuo H. Histological observations and the process of ultrasound contrast agent enhancement of tissue plasminogen activator thrombolysis with ultrasound exposure. Abstract of *Jpm Circ J 1999;* 63:478–484.

Francis CW, Onundarson PT, Carstensen EL, Blinc A, Meltzer RS, Schwarz K, Marder Vj. Enhancement of fibrinolysis in vitro by ultrasound. Abstract of *J Clin Invest 1992;* 90:2063–2068.

Suchkova V, Siddiqi FN, Carstensen EL, Dalecki D, Child S, Francis CW. Enhancement of fibrinolysis with 40–kHz ultrasound. *Circulation 1998;*98:1030–1035.

Otis SM, Ringelstein EB. The transcranial Doppler examination: principles and applications of transcranial Doppler sonography. In: Tegeler CH, Babikan VL, Gomez Cr. Neurosonology. St Louis: *Mosby, 1996.* Pp113–129.

Blinc A, Francis CW, Trudnowski JL, Carstensen EL. Characterization of ultrasound–potentiated fibrinolysis in vitro. *Blood 1993;*81:2636–2643.

Aronowski J, Samways E, Strong R, Rhoades Hm, Grotta JC. An alternative method of quantitation of neuronal damage after experimental middle cerebral artery occlusion in rats: analysis of behavioral deficit. *J. Cerev Blood Flow Metab 1996;*16:705–713.

Alexandrov AV, Demchuk AM, Felberg RA, Christou I, Barber PA, Burgin WS, Malkoff M, Wojner AW, Grotta JC.High rate of complete recanalization and dramatic clinical recovery during TPA infusion when continuously monitored by 2 MHz transcranial Doppler.*Stroke 2000:*31:610–614.

Demchuk, A. et al. *Journal of Neuroimag 2000*;10:1–12.

Demchuk, A. et al. *Stroke* 2000;31:140–146.

Burgin SW, Felberg RA, Demchuk AM, Christou I, Grotta JC, Alexandrov AV. Ultrasound criteria for middle cerebral artery recanalization: an angiographic correlation. *Stroke 2000;*31:1128–1132.

Fink M, Time–Reversed Acoustics. *Scientific American,* Nov. 1999: Pp 91–97.

Niwicki A, Kowalewski T, Secomski W, Wojcik J. Estimation of acoustical streaming: theoretical model, Doppler measurements and optical visualisation. *European Journal of Ultrasound 7* (1998) 73–81.

Other nonthermal mechanisms: acoustic radiation force and streaming. *Ultrasound in Med. & Biol.* vol. 24, Supplement 1, Pp 523–528, 1998.

Study suggests ultrasound may speed clot–busters' effect in stroke. *Doctor's Guide to Medical & Other News.* Other News. E–mail Edition Pp 1–3.

Zauhar G, Starritt HC, Duck FA. Studies of acoustic streaming in biological fluids with an ultrasound Doppler technique. *The British Journal of Radiology,* Mar. 1998 Pp 297–302.

* cited by examiner

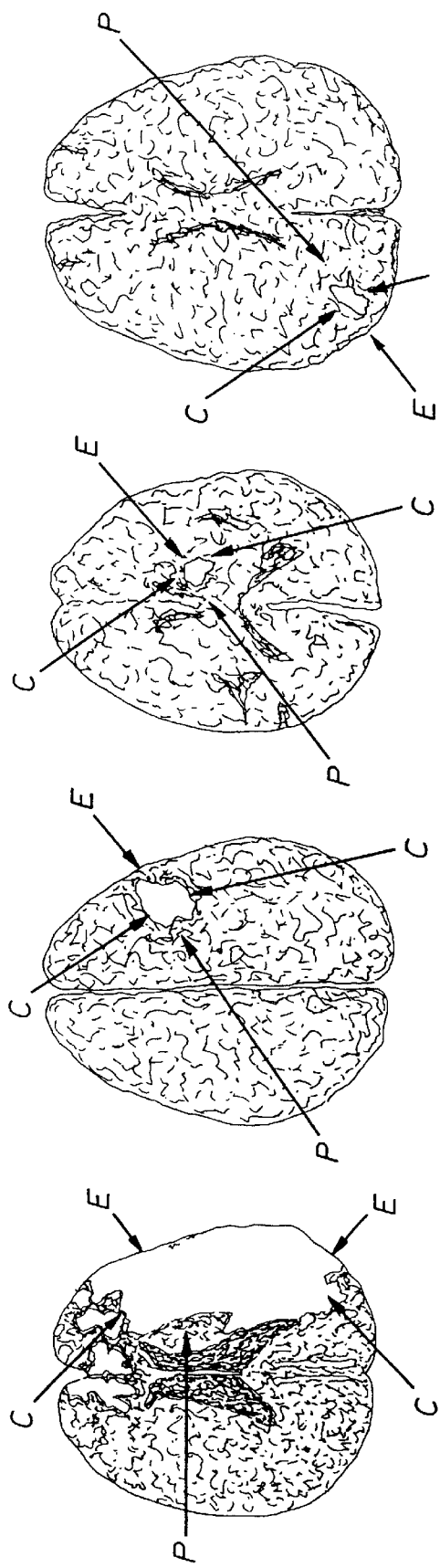

THERAPEUTIC METHODS AND APPARATUS FOR USE OF SONICATION TO ENHANCE PERFUSION OF TISSUE

FIELD OF THE INVENTION

The field of the invention lies in ultrasound methods and apparatus for reducing tissue damage from ischemia by means of insonation. The invention pertains to therapeutic medical systems and, more particularly, to the therapeutic use of ultrasound methods and apparatus for reducing tissue damage from ischemia.

BACKGROUND OF THE INVENTION

The insonation of the instant invention has the goals of reducing edema and promoting microcirculation, recanalization, collateral and interstitial flow, and delivery of lytic agents to clots located in supplying arteries, as well as delivery of nutrients and/or drugs to the ischemic tissue. Goals of the apparatus and method may even extend to clot destruction through a re-enforced focusing of multiple beams.

More particularly, in accordance with the methods and apparatus of the instant invention, at least a portion if not all of an organ affected by ischemia is exposed to low frequency low power ultrasound, preferably generated by a plurality of transducers from directions spanning at least a 45° angle and over at least a one minute period, preferably over an hour period, more preferably over many hours. The system can also be used to maintain and enhance biological tissue function and viability in a setting of reduced perfusion by exposure to ultrasound energy transmission.

The principles taught, demonstrated and tested herein use the reduction of tissue damage from brain ischemia as a preferred embodiment, brain ischemia offering a most difficult test case. The bone attenuation of ultrasound has not received extensive consideration in the art. The effect of the cranium bone structure, in particular, has presented itself as a significant obstacle to insonation of the brain.

Addressing brain ischemia in general, a significant reduction in cerebral blood flow leads to brain ischemia and, if untreated, may cause stroke leading to permanent tissue damage (infarction), severe disability, and, in many cases, death. In particular, an ischemic stroke occurs when a thrombus obstructs cerebral arteries. Systemically-induced thrombolysis with intravenous tissue plasminogen activator (TPA) (see *The National Institutes of Neurological Disorders and Stroke rt-PA Stroke Study Group. Tissue plasminogen activator for acute ischemic stroke. N. Engl J Med.* 1995;333:1581–1587) is the only effective therapy practiced today to reduce damage from ischemic stroke.

Although intravenous tPA improves the outcome of stroke patients (see *The National Institutes of Neurological Disorders and Stroke rt-PA Stroke Study Group. Tissue plasminogen activator for acute ischemic stroke. N Engl J Med.* 1995;333:1581–1587) recanalization is not achieved in a significant portion of arterial occlusions (74% of cerebral arteries) when tPA is given alone (see del Zoppo G J, Poeck K, Pessin M S, Wolpert S M, Furlan A J. Ferbert A, Alberts M J, Zivin J A, Wechsler L, Busse O, Greenlee R, Brass L, Mohr J P, Feldmann E, Hacke W. Kase C S, Biller J, Gress D, Otis S M. *Recombinant tissue plasminogen activator in acute thrombotic and embolic stroke. Ann Neurol.* 1992; 32:78–86).

Ultrasound in the low MHz-kHz frequency range (see Akiyama M, Ishibashi T. Yamada T. Furuhata H. *Low-frequency ultrasound penetrates the cranium and enhances thrombolysis in vitro.* Abstract of *Neurosurgery* 1998; 43:828–832 and Behrens S, Daffertshofer M, Spiegel D, Hennerici M. *Low-frequency, low-intensity ultrasound accelerates thrombolysis through the skull.* Abstract of *Ultrasound Med Biol* 1999; 25:269–273) has been shown to promote thrombolysis in vitro models of cerebral arterial thrombosis by substantially increasing the thrombolytic effect of tPA.

In other experiments, ultrasound exposure has been shown to cause various changes such as reversible disaggregation of uncrosslinked fibrin fibers (see Abstract of Braaten J V, Goss R A, Francis C W. *Ultrasound reversibly disaggregates fibrin fibers. Thromb Haemost* 1997;78:1063–1068), microcavity formation in the shallow layer of thrombus (see Abstract of Kondo I, Mizushige K, Ueda T. Masugata H, Ohmori K, Matsuo H. *Histological observations and the process of ultrasound contrast agent enhancement of tissue plasminogen activator thrombolysis with ultrasound exposure. Jpn Circ J* 1999;63:478–484), and increasing the enzymatic transport of tPA improving uptake and penetration of tPA into clots (see Abstract of Francis C W, Onundarson P T, Carstensen E L, Blinc A, Meltzer R S, Schwarz K, Marder V J. *Enhancement of fibrinolysis in vitro by ultrasound. J Clin Invest* 1992; 90:2063–2068).

It has been concluded that ultrasound promotion of drug-induced lysis does not appear to be mediated by thermal or cavitational effects (see Abstract of Suchkova V, Siddiqi F N, Carstensen E L, Dalecki D, Child S, Francis C W. *Enhancement of fibrinolysis with 40-kHz ultrasound. Circulation* 1998;98:1030–1035).

A 2 MHz pulsed wave ultrasound is used in the diagnostic equipment for cerebrovascular studies (see Otis S M, Ringelstein E B. *The transcranial Doppler examination: principles and applications of transcranial Doppler sonography. In:* Tegeler C H, Babikian V L, Gomez C R. Neurosonology. St Louis:Mosby, 1996. Pp 113–129). Some have suggested that the ideal frequency for ultrasound mediated thrombolysis appears to be the 1–2.2 MHz range (see Abstract of Blinc A, Francis C W, Trudnowski J L, Carstensen E L. *Characterization of ultrasound-potentiated fibrinolysis in vitro. Blood* 993;81:2636–2643). However, this level of insonation may not deliver sufficient energy to disrupt a brain clot mechanically, due to the tremendous attenuation of ultrasound through the skull bone (see Abstract of Akiyama M, Ishibashi T. Yamada T. Furuhata H. *Low-frequency ultrasound penetrates the cranium and enhances thrombolysis in vitro.* Cite above *Neurosurgery* 1998; 43:828–832 and Behrens S, Daffertshofer M, Spiegel D, Hennerici M *Low-frequency, low-intensity ultrasound accelerates thrombolysis through the skull. Ultrasound Med Biol* 1999;25:269–273).

The impact of continuous exposure to ultrasound on cerebral ischemic tissue and on cerebral clots in human patients, in vivo, has not been studied before. Its utility, thus, has not previously been raised to the level reached by the instant demonstration. The instant invention is based upon both human and experimental animal model studies involving cerebral ischemic tissue. Methods and techniques suggested and indicated by the undertakings of the instant studies, however, are also applicable, as will be readily appreciated, to other tissue and organs.

Eggleton and Fry (see Eggleton R C, Fry F J. U.S. Pat. No. 3,951,140. Apr. 20, 1976) teach that low intensity ultrasound can be used to potentiate healing of various biological tissues, in particular the heart, by means of combating tissue swelling, increasing permeability of biological membranes, and inducing interstitial flow of fluids under radiation pressure (microstreaming). Although their patent discloses apparatus and method for therapeutic ultrasound insonation of ischemic tissue and energy transmission to infarcted tissue (in particular, the heart), their approach does not extend to teaching the identification of normal donor tissue for promoting collateral and/or interstitial flow, or to teaching methods and apparatus for utilizing beams that span at least 45°, or to utilizing beams that expose an entire organ or tissue to ultrasound.

No specific methods or ultrasound devices are taught by the prior art to particularly penetrate bones or to utilize vasculature in order to sonicate tissue at risk, as well as to sonicate normal tissue of the organ, all designed to limit tissue damage from ischemia. Jolez and Hynynen (see Jolesz F A, Hynynen K U.S. Pat. No. 5,752,515. May 19, 1998) disclose noninvasive methods and apparatus for delivery of various compounds through a blood brain barrier using ultrasound-induced cavitation and heating in a small target area (1 $mm^3$–1 $cm^3$). However, such hyperthermia exacerbates ischemic brain damage, and such cavitation is an adverse biological effect of ultrasound which should be avoided whenever possible unless focal tissue destruction is taught.

In sum, previously published papers and patents do not disclose the specific methods and apparatus taught herein for marshaling the impact of low frequency low power ultrasound exposure on ischemic tissues, vascular structure and/or normal donor tissue to mitigate permanent tissue damage. It is an object of this invention to provide detailed methods and apparatus for reducing biological tissue damage from ischemia by means of continuous insonation through intact skin and around and/or through bone which should result in the reduction of edema, promotion of microcirculation, interstitial fluid flow, recanalization, collateral flow and the delivery of lytic agents to clots located in supplying arteries as well as the delivery of nutrients, therapeutic substances and/or drugs to ischemic tissues. Even clot disruption is a possible modality. These and other objects are attained by the invention which provides methods and ultrasound apparatus for reducing biological tissue damage from ischemia and ischemia induced complications.

SUMMARY OF THE INVENTION

The methods and apparatus of the instant invention are demonstrated using brain ischemia as a prime, and a most difficult, example. The methods according to one aspect of the invention include applying ultrasound waves generated by multiple transducers to various portions of skin surface (areas extending in some cases to total areas exceeding an entire organ surface, as for instance to 90% of a skull surface) in order to expose supplying and draining vasculature, ischemic tissue and potential donor tissue, as a source of collateral flow and nutrients, (including potentially the entire organ) to low-power (<1000 mW) low-frequency ultrasound. In the setting of brain ischemia, one experimental model as well as human studies indicate that ultrasound penetration through the skull can be sufficient to expose target tissue to acoustic pressure gradients and to detect residual flow around a clot in intracranial arteries. Studies indicate that ultrasound frequencies from 1 KHz to 10 MHz might be beneficially used, with the duration of sonication varying from 1 minute to 24 hours and with burst mode repetition varying from 0.1 Hz to continuous and with power varying from 1 mW to 1000 mW.

In one aspect of the invention, microstreaming is induced in the tissues which, utilizing the method and apparatus taught herein, may be harnessed to reduce tissue edema, deliver energy to ischemic cells, promote collateral and interstitial flow and promote drug/nutrients delivery to ischemic tissues. In a further aspect, the invention provides methods and apparatus that combine targeting and fluid, nutrient and drug delivery systems to the ischemic tissue areas with mechanical agitation of other targeted tissues, including clots, located in the vasculature. Viewed from another further aspect, the invention provides methods of maintaining biological tissue viability in a setting of reduced perfusion by exposing the entire ischemic tissue or organ to multi-directional ultrasound energy transmission. The invention further provides methods and apparatus that expose an ischemic organ to a plurality of ultrasonic waves, simultaneously and/or sequentially, with different frequencies, powers, pulse configurations and synchronization, to achieve enhancement of thrombolysis, edema reduction, energy delivery, promotion of collateral and interstitial flow, recanalization and an increase of venous outflow.

The invention includes a source of acoustic waves and apparatus for attachment to the source of acoustic waves. The apparatus comprises a plurality of transducer probes and a frame. The frame is structured such that the probes can be arranged to at least partially, and possibly completely, surround a human organ, targeted at selected tissues, and be held there in place. At least two acoustic beams produced by transmitting probes should be focusable to span at least a 45° angle. Speaking more precisely, in order to reduce what is in reality three dimensions into two dimensional language, for ease of understanding, since two beams may not precisely lie in a single plane, in order to measure a 45° angle it should be understood that the beams may need to be projected to a common plane. The closest common plane would be selected.

Preferably an acoustic beam source will include means for firing acoustic beams through its probes sequentially. The source also preferably includes means for emitting at least two beams of relatively narrow width, focusable to approximately intersect. The source apparatus preferably includes means for synchronizing emissions from two or more focused relatively narrow beams to effect, for instance, a beam reinforcement in at least a portion of an area of an intersection.

Preferably an acoustic source apparatus includes means for varying the power of a plurality of beams, as from 1 mW to 1000 mW, for varying the frequency of a plurality of beams, as from 1 KHz to 10 MHz, and for varying the pulse rate of a plurality of beams, as from 10 per second to continuous. Preferably the apparatus will include means for receiving reflected waves for diagnostic purposes with at least one probe, and possibly more.

The invention includes a method for the therapeutic use of ultrasound to enhance perfusion of tissue. The method includes identifying, in at least one organ tissue zone, a boundary between at least one normal tissue zone and one ischemic tissue zone. The method includes arranging a plurality of probes to direct acoustic beams, focused to span an angle of at least 45°, into the organ tissue zone, with at least one beam or beam set passing through the boundary to induce fluid motion across the boundary. The method includes applying insonation through the probes to the tissue zone for at least 1 minute, including preferably several hours, and up to 24 hours or more, and acoustic transmission monitoring, at least periodically, for indicia of perfusion for at least a portion of the tissue zone.

The method may include testing indicia of probe effectiveness and selecting probes to be activated based upon the testing. The testing may also indicate the selection of direction or focusing for beam propagation. Probes may be mechanically and/or electronically aligned and activated with mechanical or electronic steering. Test pulses emitted at different frequency ranges may permit estimating penetration through bone by an indicia of the strength of return echoes. The method may also include selecting position and direction for at least one beam based upon vasculature structure and/or bone structure around at least one zone. The method may also include firing acoustic beams sequentially and/or emitting at least two beams of relatively narrow focus and steering the beams to intersect. The method may include synchronizing emissions from at least two beams to effect a positive beam reinforcement in at least a portion of an area of intersection. Preferably the method includes producing a plurality of beams with independently variable power levels, independently variable frequency and independently variable pulse rate.

BRIEF DESCRIPTION OF THE DRAWINGS

A better understanding of the present invention can be obtained when the following detailed description of the preferred embodiment is considered in conjunction with the following drawings, in which:

FIG. 15 shows typical findings on brain magnetic resonance imaging (MRI) that can be used to identify arterial territories and their combinations involved in ischemia for tissue targeting by operators of the ultrasound device.

DETAILED DESCRIPTION OF PREFERRED EMBODIMENTS

Research Data Supporting the Invention:Laboratory Investigations

The following effect was evaluated 1 hour exposure to simple pulsed wave ultrasound on the infarct volume measured in a reproducible animal model of focal cerebral ischemia (animal model of ischemic stroke in humans) previously developed in a laboratory (see Aronowski J. Samways E, Strong R, Rhoades H M, Grotta J C. *An alternative method of quantitation of neuronal damage after experimental middle cerebral artery occlusion in rats: analysis of behavioral deficit. J Cereb Blood Flow Metab* 1996;16:705–713). An experimental model with permanent arterial occlusion was used to eliminate the effects of reperfusion.

Figure 1:
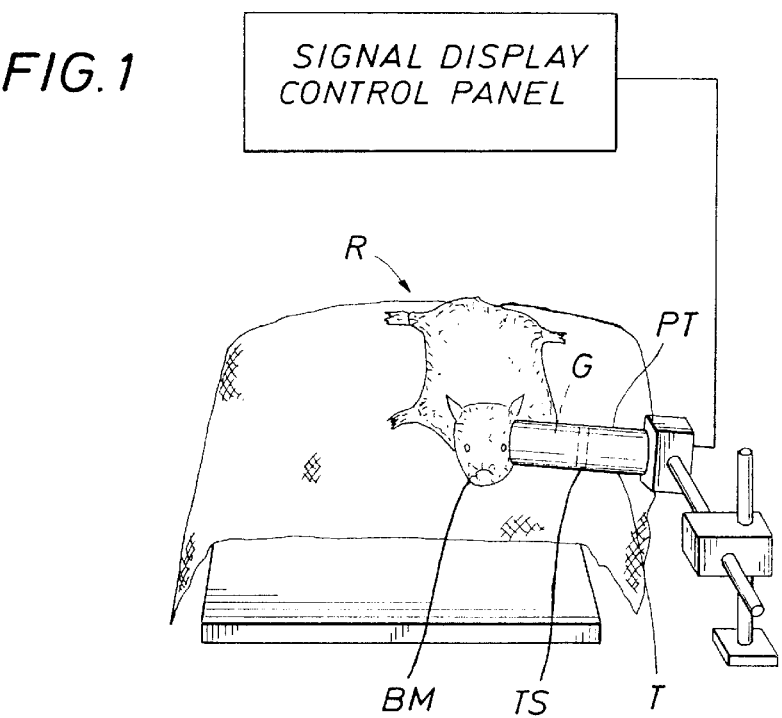
FIGS. 1 and 1A show how ischemic rat brain was exposed to ultrasound in laboratory studies.
Figure 1A:
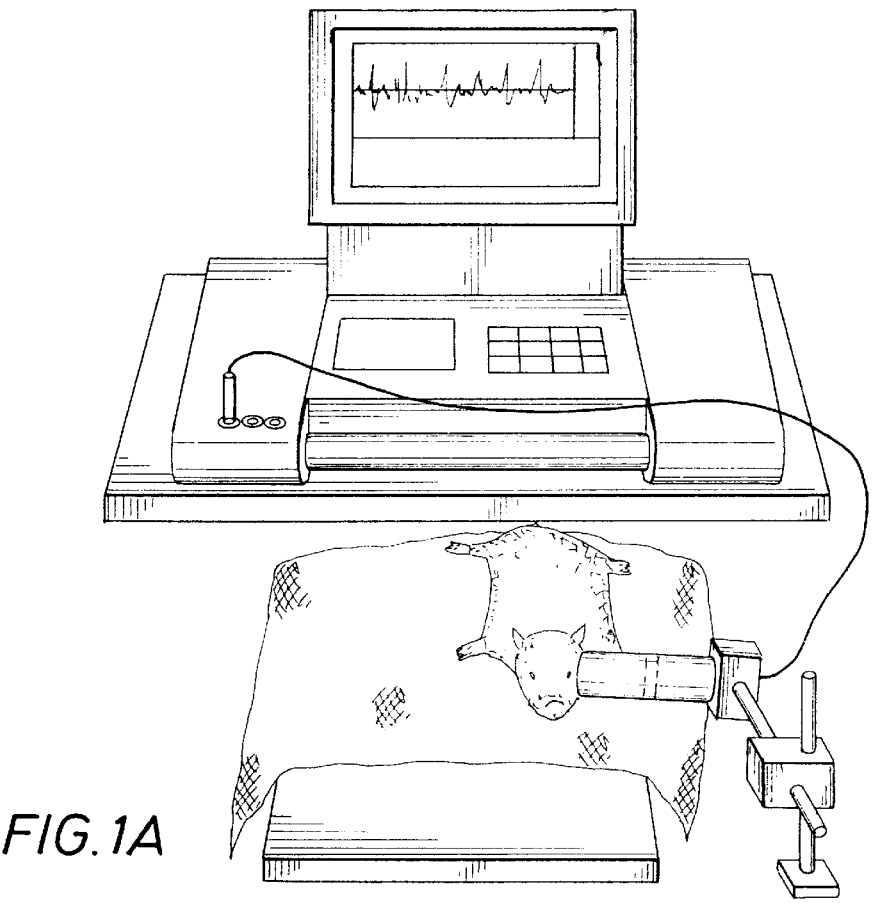
Figure 2:
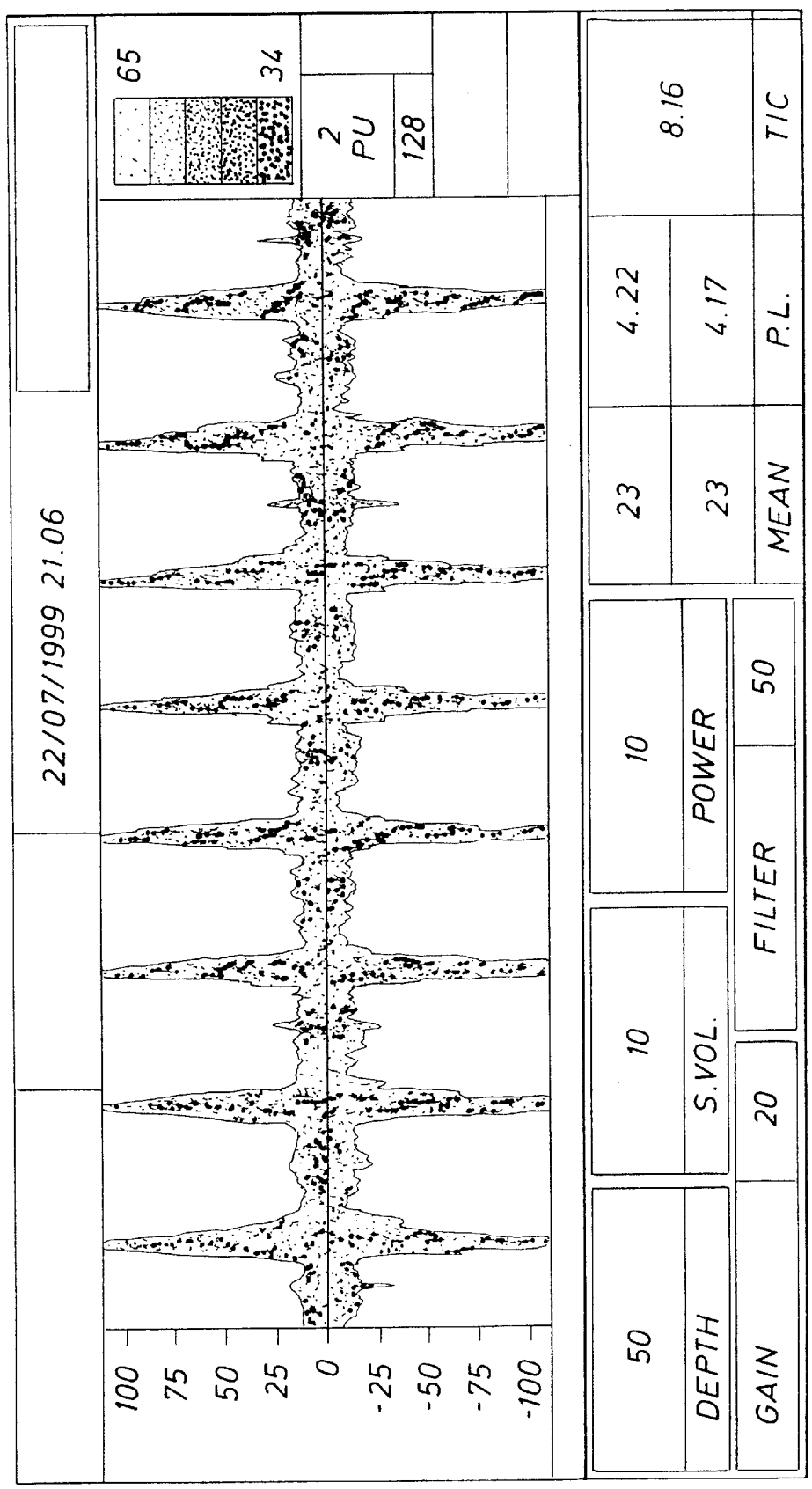
FIG. 2 represents a sample of arterial flow signals detected at 5 cm depth of insonation during rat brain exposure to ultrasound.

The transducer dimension, ultrasound frequency, power levels of exposure and depth of insonation were those used to insonate humans (see Otis S M, Ringelstein E B. *The transcranial Doppler examination: principles and applications of transcranial Doppler sonography. In:* Tegeler C H, Babikian V L, Gomez C R. *Neurosonology. St Louis: Mosby,* 1996. Pp113–129). Transcranial insonation was performed with a 2 MHz pulsed wave ultrasound generated with pulse repetition frequency of 5.2 KHz. One ultrasound transducer T with a radius of 1 cm was placed at the level of temporal bone between the ear and eye. The distance from the transducer surface TS to the brain midline structures BM was 5 cm (FIG. 1). The transducer emitting area covered an entire side of the rat skull, between the eye and most of the ear, thereby exposing an entire lateral brain surface to the ultrasound beam. The transducer was placed in a plastic tube PT and a transmission gel G was used to fill the space between the transducer and rat skin, as is known in the art. The gel was injected into the plastic tube without major air bubble formation. The depth of insonation was set at 5 cm with sample volume of 1 cm. Exposure to ultrasound lasted 1 hour. In the first group of animals, the power of 128 mW was used. In the second group, power was decreased to 10 mW. This lower power level was selected since minimum power is recommended for transorbital and other examinations in humans and a 90% attenuation of the full power signal has been indicated as possibly present when insonation through a human skull is performed. Brief detection of arterial pulsations was possible in all animals at depths of insonation 4.5–6.5 cm which confirmed successful penetration of ultrasound through the skull (FIG. 2) for both power levels. Arterial flow signals were detected with the amplitude A of pulsations reaching 100 cm/sec and the heart rate HR of 120–150 beats/per minute. Control animals also had permanent middle cerebral artery (MCA) occlusion but received no ultrasound exposure. FIG. 1A illustrates the TCD Multidop-T DWC equipment utilized.

Results

Figure 3:
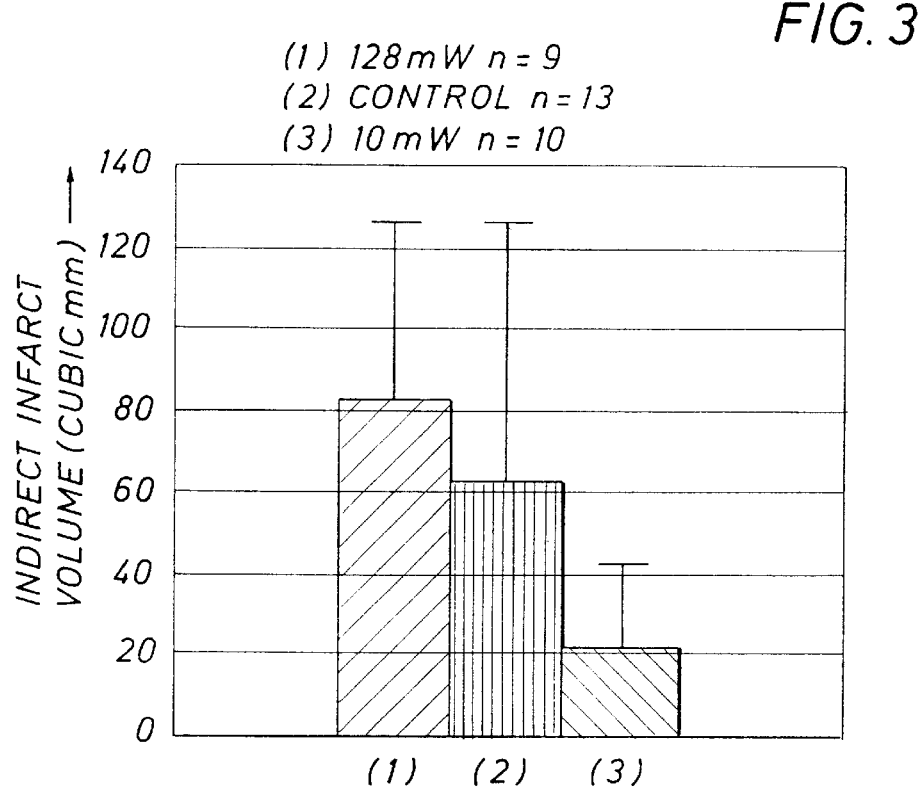
FIG. 3 shows a bar graph representing indirect infarct volume ($mm^3$) produced by focal ischemia in rats treated with (1) 128 mW or (3) 10 mW insonation as compared to untreated ischemic control (2) measurements in animal groups.
Figure 4:
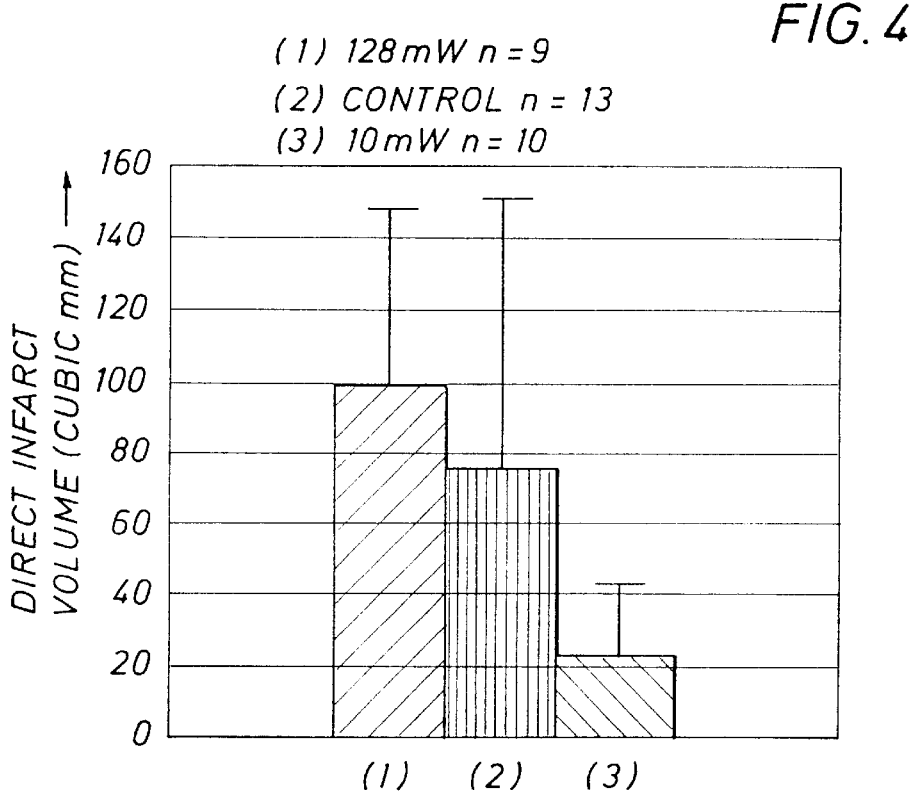
FIG. 4 shows a bar graph of the direct infarct volume ($mm^3$) produced by focal ischemia in rats treated with (1) 128 mW or (3) 10 mW insonation as compared to untreated ischemic control (2).
Figure 5:
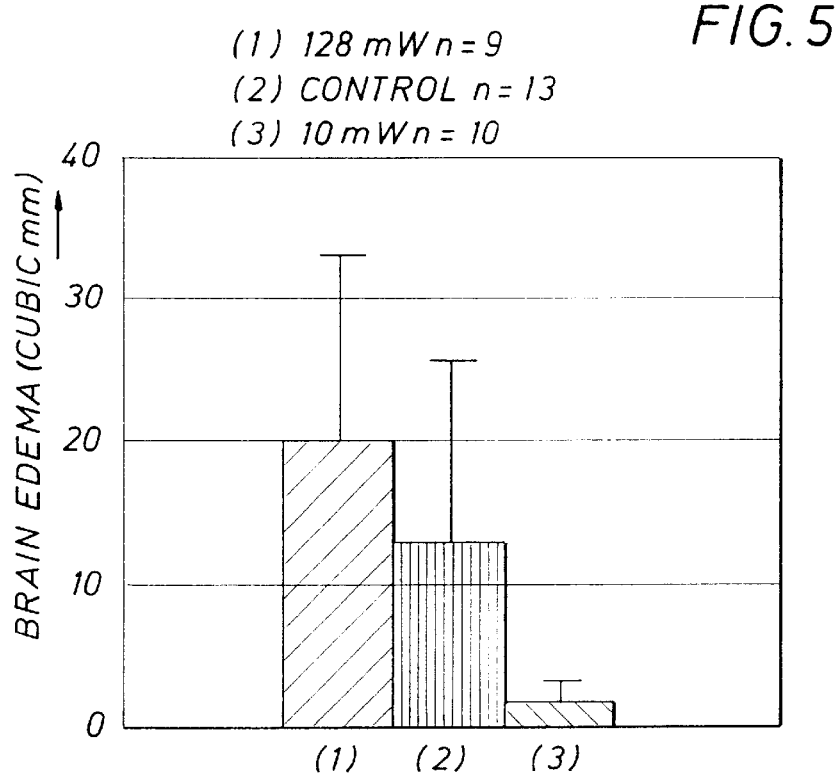
FIG. 5 shows a bar graph of the brain edema measurements in animal groups.

Indirect infarct volume in the control ischemic group was 62.9±37 mm$^3$, in the 128 mW group 82.3±44.0 mm$^3$, and in the 10 mW group 21.4±18.3 mm$^3$ (p=0.0039 different from control). Direct infarct volume measurements in the control group were 75.3±46.5 mm$^3$, in the 128 mW group 99.2±49.17 mm$^3$, and in the 10 mW 22.5±20.4 mm$^3$ (p=0.0031 different from control). Edema measurements were 12.7±12.1 mm$^3$ in controls, 20.0±13.0 mm$^3$ in the 128 mW group, and 1.56±3.4 mm$^3$ in the 10 mW group (p=0.01) (FIGS. 3–5). This indicates that the 128 mW power level is too high for the rat, but that continuous simple insonation through the skull with a lower power level dramatically reduced tissue infarction.

Figure 6:
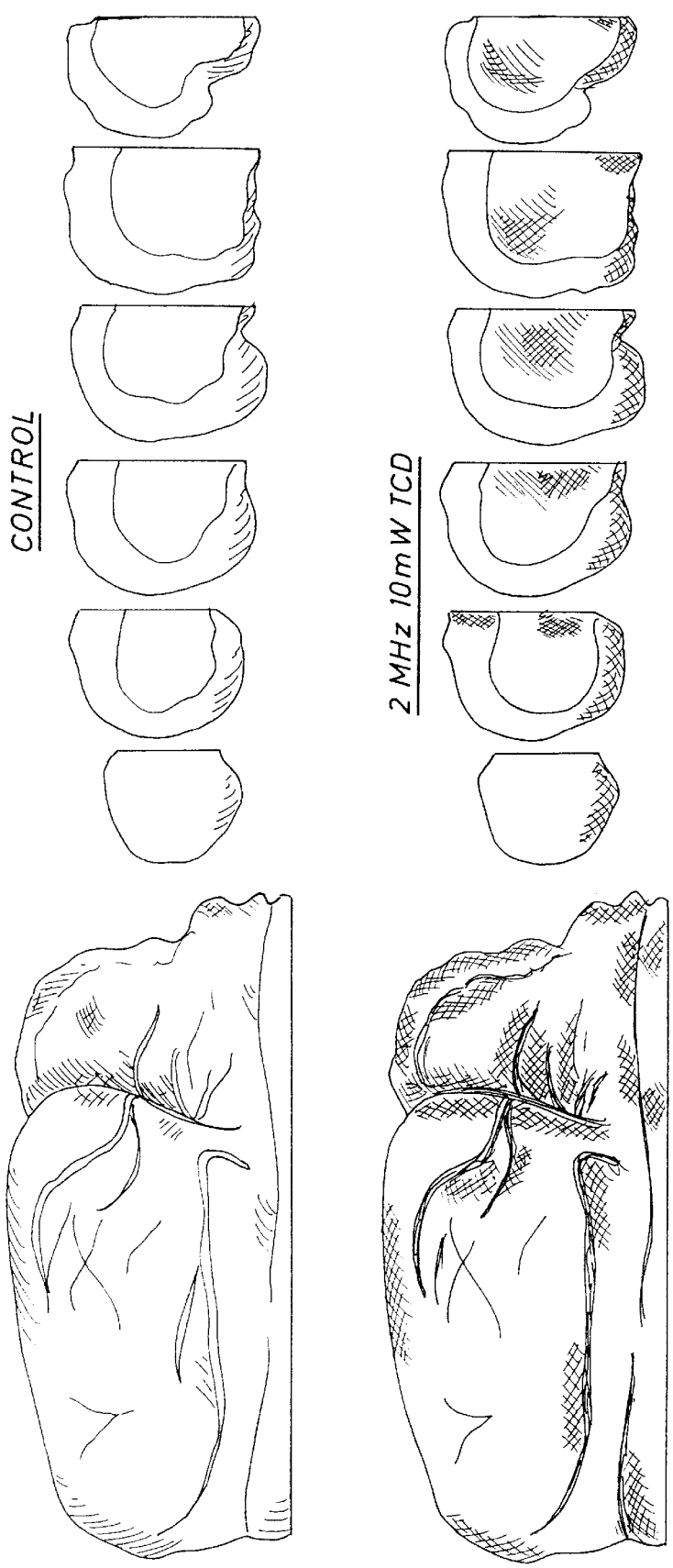
FIG. 6 is a digital (color) photograph of water-soluble ink distribution in the whole rat brain and coronal cross-sections in a control rat and a rat exposed to 10 mW 2 MHz ultrasound, with left images offering lateral views of the ischemic left MCA territory and right images offering coronal serial (rostro-caudal) cross-section.

A water-soluble ink was injected in the femoral artery at 30 minutes after permanent middle cerebral and common carotid artery occlusion in a control animal CA and in a rat R sonicated for 1 hour with 10 mW pulsed wave ultrasound. Both animals were sacrificed at 2 hours of permanent MCA occlusion. The left image of FIG. 6 show lateral views of the ischemia left MCA territory. Right images show serial coronal cross-section. More cortical deposition of ink distal to the site of occlusion was found at visual macroscopic examination (FIG. 6) in the MCA branches as well as cortical and sub-cortical areas of the brain exposed to ultrasound or compared to control.

Clinical Human Investigations:

Consecutive patients, who were treated with intravenous TPA (see Background of the Invention) and received continuous 2 MHz transtemporal transcranial Doppler (TCD) "monitoring" between 07/98 and 09/99, were included into the study (see Alexandrov A V, Demchuk A M, Felberg R A, Christou I, Barber P A, Burgin W S, Malkoff M, Wojner A W, Grotta J C. *High rate of complete recanalization and dramatic clinical recovery during TPA infusion when continuously monitored by* 2 MHz *transcranial Doppler.Stroke* 2000;31:610–614). TPA was given in a standard 0.9 mg/kg dose (10% bolus, 90% continuous infusion over 1 hour) to patients presenting within the first 3 hours after symptom onset. In selected patients presenting between 3–6 hours of onset or with other risk for hemorrhagic complications, TPA was given in a dose of 0.6 mg/kg (15% bolus, 85% continuous infusion over 30 minutes). This experimental protocol was approved by the University of Texas Committee for Protection of Human Subjects.

A standard TCD examination was performed in the emergency room before TPA bolus using a single channel unit with full power settings (see below). No delay in TPA administration was experienced as a result of the ultrasound examination. TCD was used to identify the site of intracranial occlusion following previously published diagnostic criteria (see Demchuk, A. et al. *Journal of Neuroimag* 2000;10:1–12) attached. Once the occlusion was diagnosed by handheld examination, the presumed clot location and residual flow around it was determined by the presence of abnormal flow signals (minimal, blunted, or dampened waveforms) (see Demchuk, A. et al. *Stroke* 2000;31:140–146) attached. Continuous ultrasound monitoring of the flow signals at the presumed clot location was initiated. See FIG. 7.

To select the depth for single gate monitoring, the following algorithm was used.

Distal M1–M2 MCA occlusion: the residual flow signals had to be found at 40–45 mm and the monitoring depth was set accordingly.

Proximal M1 MCA occlusion: monitoring was performed at 55–60 mm.

Asonic MCA occlusion 1: If no signal could be obtained from the entire stem of an occluded artery, the flow void depth closest to the normal signal was selected. For example, monitoring depth was set at 60–65 mm if no MCA signals were found in the presence of a normal anterior cerebral artery.

Asonic MCA occlusion 2: If no flow signals were detected from the distal part and the abnormal signals were obtained at the proximal part of the MCA, the monitoring depth was set at the depth displaying the abnormal signal closest to the signal void depths.

ICA occlusion: If the internal carotid artery (ICA) was occluded without tandem proximal MCA occlusion, the distal MCA flow signal was monitored at 40–45 mm.

T-type ICA occlusion: If the terminal ICA was occluded with no or minimal signals from M1 and A1 segments, the MCA origin was monitored at 65 mm.

Basilar artery occlusion: a similar algorithm was applied to select depths of 80 mm (proximal BA) or 100 mm (distal BA).

Normal pre-treatment TCD: If a lacunar stroke was clinically suspected, mid MCA depth of 56 mm was used for monitoring. If a small cortical stroke was suspected, distal MCA depth of 35–40 mm was used for monitoring.

Figure 8B:
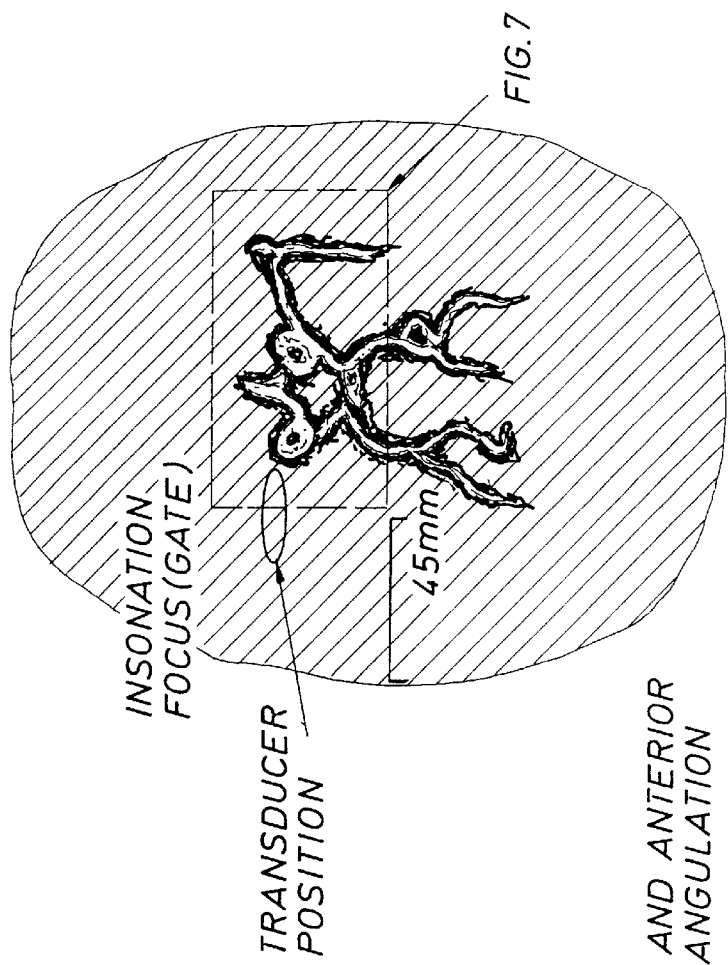
FIG. 8 shows target area for continuous ultrasound exposure of human cerebral arteries in patients with ischemic stroke, with TCD monitoring of MCA residual flow signals (from Strobe 2000; 31:p 612).
Figure 8A:
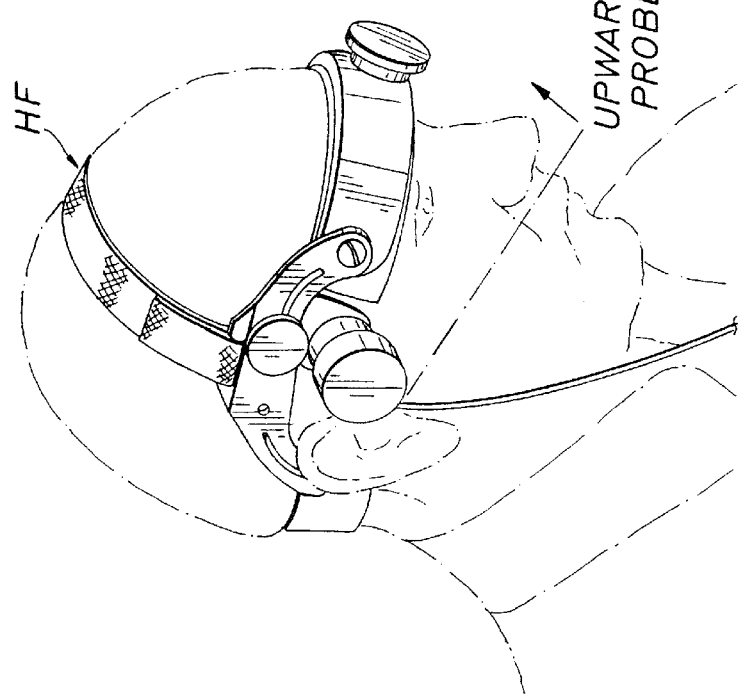

The sample volume (gate) was set at 11.8–15 mm. The power was set at maximum (or 128 mW) for the duration of monitoring. For patients with anterior circulation occlusion, the transducer was tightly fixed in position using a head-frame HF to maximize sound energy transmission and to maintain a constant angle of insonation (FIG. 8). For patients with BA occlusion, handheld monitoring was performed via the transforaminal window.

TCD monitoring was performed during the entire TPA infusion under direct visual control of the investigators. If any flow signal changes occurred, these data were interpreted on line and the timing of change was documented. The flow signals at the proximal and distal arterial segments were documented at the end of TPA infusion and TCD monitoring was discontinued at this point.

Recanalization was graded as complete, partial, or none according to previously validated criteria (see Burgin S W, Felberg R A, Demchuk A M, Christou I, Grotta J C, Alexandrov A V. *Ultrasound criteria for middle cerebral artery recanalization: an angiographic correlation. Stroke* 2000;31:1128–1132 attached). Complete recanalization. was diagnosed when a normal waveform or a low resistance stenotic signal appeared at the selected depth of insonation. If a proximal arterial segment was monitored, the continuation of normal or low resistance stenotic flow towards the distal arterial segment was confirmed. If the abnormal signals were still seen at the distal portion, partial recanalization was diagnosed. No change in the abnormal flow signals indicated that no recanalization has occurred. Re-occlusion was diagnosed when the abnormal flow signals worsened in comparison to the baseline study or after a transient flow signal improvement during TPA infusion.

The National Institutes of Health Stroke Scale (NIHSS) scores were obtained before and after TPA infusion by a neurologist not involved in TCD. Outcome measurements included the NIHSS scores at the end of TPA infusion, and at 24 hours, and modified Rankin Scale scores at follow-up. The following four measures of clinical recovery were used. "Dramatic recovery" was defined as decrease of the total NIHSS score to less than 3 at the end of TPA infusion. "Early neurological improvement" was defined as reduction by $\geq 10$ points on the total NIHSS score or complete recovery. "Improvement" was defined as the reduction of the total NIHSS score by $\geq 4$ points or complete recovery. "Worsening" was defined as increase by 4 points or more on the total NIHSS score.

At follow-up, a neurologist obtained modified Rankin scores at an outpatient visit or using a structured phone interview. Statistical analysis included the Chi-square test and coefficient of contingency to establish an association between recanalization and clinical recovery.

Results:

40 patients were studied. The mean age was 70±16 years (range 32–93 years). Baseline stroke severity was 18.6±6.2 NIHSS points (median 19 points, range 6–33). TPA bolus was given at 132±54 minutes from symptom onset including 6 patients treated with 0.6 mg/kg dose given 120 to 360 minutes from time the patient was last known normal. At the pre-bolus TCD examination, the MCA was occluded in 30 patients (75%), ICA in 11 patients (28%); and basilar in 3 patients (8%). Multiple occlusions involving ICA and MCA were found in 7 (18%). Four patients had no windows of insonation (10%). Only one patient (2.5%) had a normal TCD examination before the TPA bolus.

TCD monitoring started 125±52 minutes after symptom onset and continued for the duration of TPA infusion in all patients. Evidence for complete or partial recanalization on TCD was found in 28/40 patients (70% at 45±20 min after the TPA bolus was given. Complete recanalization occurred in 12 patients (30%) and partial recanalization was found in 16 patients (40%) (Table 1 below.)

TABLE 1

Clinical Recovery During TPA Infusion Combined with Continuous 2 MHz TCD Monitoring.
Clinical Recovery at the End of TPA Infusion

| Recanalization at the End of TPA Infusion by TCD | "Dramatic" Total NIHSS Score < 3 | "Partial" NIHSS Decrease b $\geq$ 4 Points | "None" No Change or Worsening |
|---|---|---|---|
| Complete | 8 | 1 | 3 |
| Partial | 0 | 7 | 9 |
| None* | 0 | 2 | 10 |

Dramatic clinical recovery was associated with complete proximal arterial recanalization during TPA infusion (C = 0.811, p $\leq$ 0.01).
Lack of improvement or worsening were due to persisting arterial occlusion on TCD.
Worsening was defined as increase in the NIHSS score by $\geq$ 4 points.
*None = no evidence for recanalization on TCD including patients with no temporal windows.

Dramatic recovery during TPA infusion (total NIHSS score <3 by the end of TPA infusion) was observed in 8 patients (20%) who all had complete recanalization on TCD. Clinical recovery was associated with recanalization ($\chi^2$= 26.3, coefficient of Contingency C=0.811, p<0.01 (Table 1)). The baseline NIHSS score of patients who experienced dramatic recovery was 13.3±5.6 points (median 13 points, range 6–22 points, age range was 32–93 years). Complete recanalization was common in patients with cardioembolic occlusion (8/17, or 47%), however this association was not significant (Table 2). If partial or complete recanalization were achieved by the end of TPA infusion, 43% of these patients (12/28) improved by $\geq$10 NIHSS points or recovered completely at 24 hours.

Overall early improvement by $\geq$10 points or complete recovery were seen in 12/40 patients (30%) at the end of TPA infusion and in 16 patients (40%) by 24 hours. An improvement by $\geq$4 points was observed in 18/40 patients (45%) at the end of TPA infusion and in 25 patients (62.5%) by 24 hours (Table 2 below.)

TABLE 2

Clinical Recovery at 24 hours after TPA Infusion.

| Improvement at 24 Hours | TPA + TCD | NINDS |
|---|---|---|
| By $\geq$ 10 NIHSS points + complete recovery | 40% | 27% |
| By $\geq$ 4 NIHSS points | 62.5% | 47% |

NINDS = NINDS rt-PA Stroke Study;
TPA + TCD = TPA infusion combined with 2 MHz Continuous TCD monitoring;
% = percent of TPA-treated patients who clinically improved in both studies.

No improvement was noted in 16 patients (40%) during TPA infusion and in 7 patients (17.5%) by 24 hours. Worsening of the neurological deficit occurred in 6 patients (15%) during TPA infusion and in 8 patients (20%) by 24 hours.

On TCD, 12 patients had persisting occlusion (30%), and 3 patients had late recanalization which occurred by 5–8 hours after stroke onset (7.5%). All these patients either worsened or had no clinical improvement within the first 24 hours. Symptomatic intracerebral hemorrhage occurred in 3/40 patients (7.5%). TCD detected complete recanalization in all three of these patients between 348 and 720 minutes which preceded neurological deterioration.

Eight patients died within the first three months after therapy (overall mortality of 20%) and 22 patients were available for long term follow-up (1.5±1.2 months). Of these, 11 patients achieved modified Rankin scores $\leq$3 (50%) including 6 patients with modified Rankin scores $\leq$1 who sustained early dramatic improvement. Two other patients who completely recanalized and improved dramatically during TPA infusion, did not sustain the improvement long term because of a subsequent re-occlusion. In the first patient, MCA recanalized 20 minutes after the TPA bolus, but re-occlusion occurred at 40 minutes, and repeat CT scan at 65 minutes showed new cortical edema formation. Several hours later this patient had late recanalization, developed a massive intracerebral hemorrhage and died. The second patient had a $\geq$50% residual basilar artery stenosis and despite receiving coumadin had a recurrent fatal basilar artery thrombosis two weeks after TPA treatment. Of 16 patients who recovered completely or improved by $\geq$10 NIHSS points by 24 hours, 3 (19%) did not sustain early improvement (2 died and 1 had late worsening of the neurological deficit with outcome Rankin score of 4 points).

The data indicate, first, that dramatic clinical improvement during TPA infusion is strongly associated with early recanalization. The recanalization rate in our study was higher than could be expected from the study by del Zoppo et al (70% vs 26%) (see del Zoppo G J, Poeck K, Pessin M S, Wolpert S M, Furlan A J, Ferbert A, Alberts M J, Zivin J A, Wechsler L, Busse O, Greenlee R, Brass L, Mohr J P, Feldmann E, Hacke W, Kase C S, Biller J, Gress D, Otis S M. *Recombinant tissue plasminogen activator in acute thrombotic and embolic stroke. Ann Neurol.* 1992;32:78–86). This suggests that continuous clot exposure to TPA with simple 2 MHz pulsed wave ultrasound indeed potentiates a thrombolytic effect in humans.

The data also indicates, second, that more patients experience early recovery by 24 hours that can be expected from the NINDS trial data (Table 2) ( see *The National Institutes of Neurological Disorders and Stroke rt-PA Stroke Study Group. Tissue plasminogen activator for acute ischemic stroke. N. Engl J Med.* 1995;333:1581–1587). Hence, 39 of 40 patients in the study had arterial occlusions on pretreatment TCD and the median NIHSS score before treatment was 19 in the study compared to 14 in the NINDS trial ( see *The National Institutes of Neurological Disorders and Stroke rt-PA Stroke Study Group. Tissue plasminogen activator for acute ischemic stroke. N. Engl J Med.* 1995;333:1581–1587). Therefore, the expected short-term outcome could have been worse in the patient population as predicted from the NINDS results (see *The National Institutes of Neurological Disorders and Stroke rt-PA Stroke Study Group. Tissue plasminogen activator for acute ischemic stroke. N. Engl J Med.* 1995;333:1581–1587). Although only 30% of the patients recanalized during TPA infusion, 62.5% improved by $\geq 4$ NIHSS points by 24 hours despite persisting occlusion. This suggests that continuous exposure to even simple pulsed wave ultrasound may promote recovery from stroke by reducing ischemic tissue damage in humans by means other than promotion of thrombolysis (i.e. by microstreaming in ischemic tissue). See references from Zauhar G. *The British Journal of Radiology*, 1998:532; Nowicki A. *European Journal of Ultrasound*, 1998:73, cited in full above. These clinical results parallel our findings in the animal model presented above.

Methods and Apparatus

Figure 7:
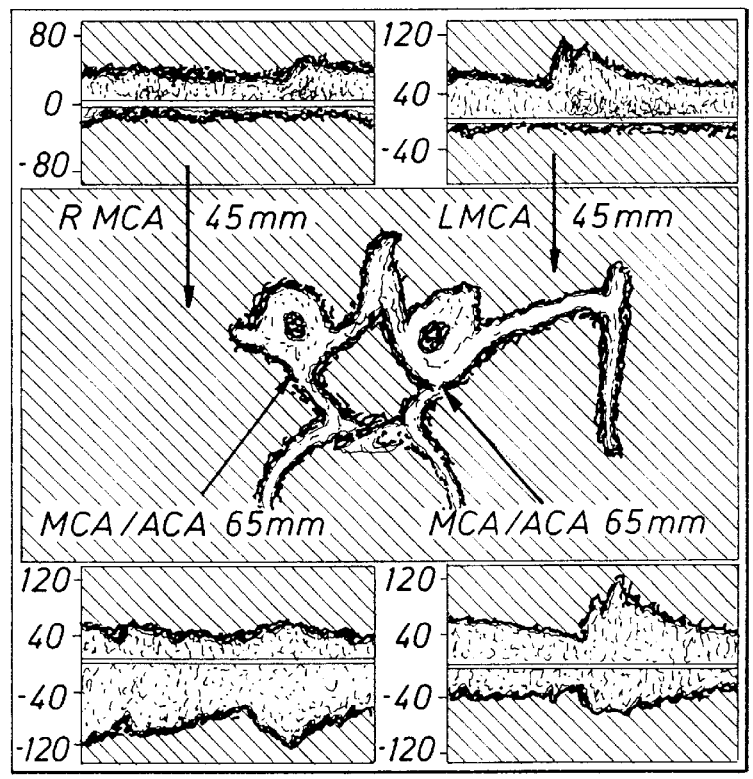
FIG. 7 represents residual flow signal findings at a clot location in cerebral arteries in a human patient with ischemic stroke (from Strobe 2000; 31: p 612).

FIGS. 7 and 8 illustrate the positioning of a probe for diagnostic and TPA infusion monitoring purposes. In particular in FIG. 7, transcranial doppler (TCD) shows a delayed right middle cerebral artery (MCA) systolic flow acceleration (above baseline). The right anterior cerebral artery (ACA) has normal flow acceleration (below baseline) and flow velocity greater than both MCA's, indicating flow diversion. These findings confirm an MCA obstruction distal to the internal carotid artery bifurcation. Magnetic resonance angiography shows flow void in the distal right M1 MCA. A blunted flow signal in the distal right M1 MCA at 45 mm depth was used to monitor TPA infusion in this case (see FIG. 8).

FIGS. 9–12 illustrate a frame structure embodiment F designed to hold emitting probes as applied to a human skull. The frame consists of adjustable parts that preferably allow:

1. Tight interface between the probes and body surface tissue to achieve effective sound transmission;
2. A renewable coupling gel layer that will maintain free-of-air interface between the body surface and probes;
3. Separate and overlapping high (for example 900 mW) and low (for example 100 mW) emitting power areas to accomplish generation of different waves with respect to organ-specific obstructed vasculature and ischemic tissue location.

The choice of frame components and probe activation will depend on organ-specific identification of clot location, ischemic tissues, and donor tissues. An appropriate frame structure might comprise an adjustable belt. A frame should exhibit at least slight flexibility and be able to be affixed around a human adult organ. Preferably, a frame offers multiple sites for attaching emitting probes.

Figure 9:
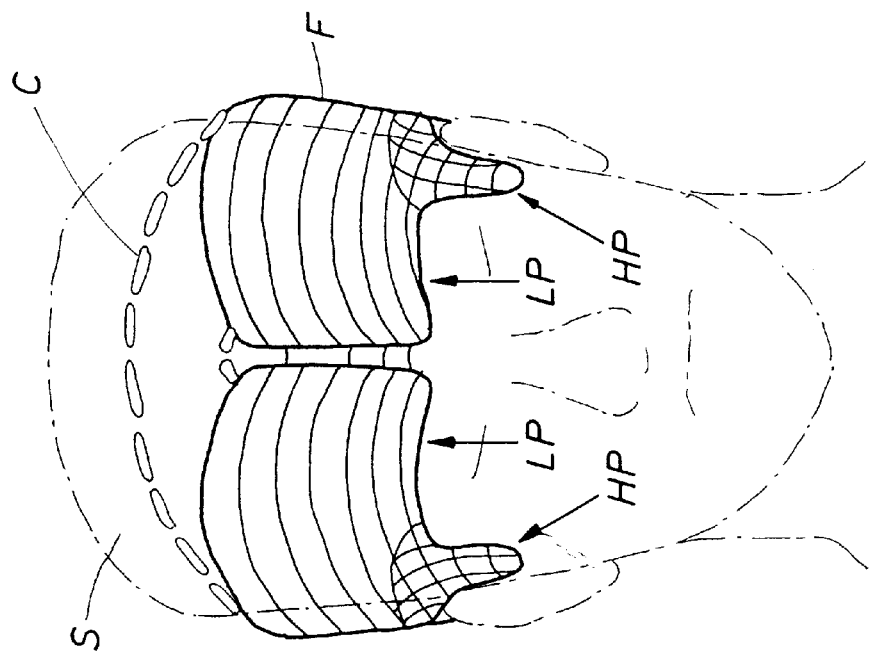
FIGS. 9–12 represent schematic drawings of a frame for holding emitting probes for the apparatus of the instant invention, adopted to be applied to skull surface portions to be exposed to ultrasound, in particular an antero-posterior view, a lateral view, a posterior view, and an antero-posterior view of skull surfaces exposed to ultrasound.

FIG. 9 shows an antero-posterior view of skull surfaces exposed to ultrasound through probes anchored upon a frame F. High power HP indicates areas of skull surface that could be exposed to thrombolysis promoting beams ("T beams"). Low power LP indicates areas that could be anticipated to be exposed to edema-reducing (E beams), collateral and interstitial flow-promoting (C beams), and pressure gradient creating (P beams) ultrasound waves. High power areas indicated correspond to the most common location of clots in human stroke (middle cerebral artery stem, terminal internal carotid artery, and basilar artery). High and low power areas may overlap to cover most of the brain surface to provide the opportunity to expose most of the affected organ to sonication.

Figure 10:
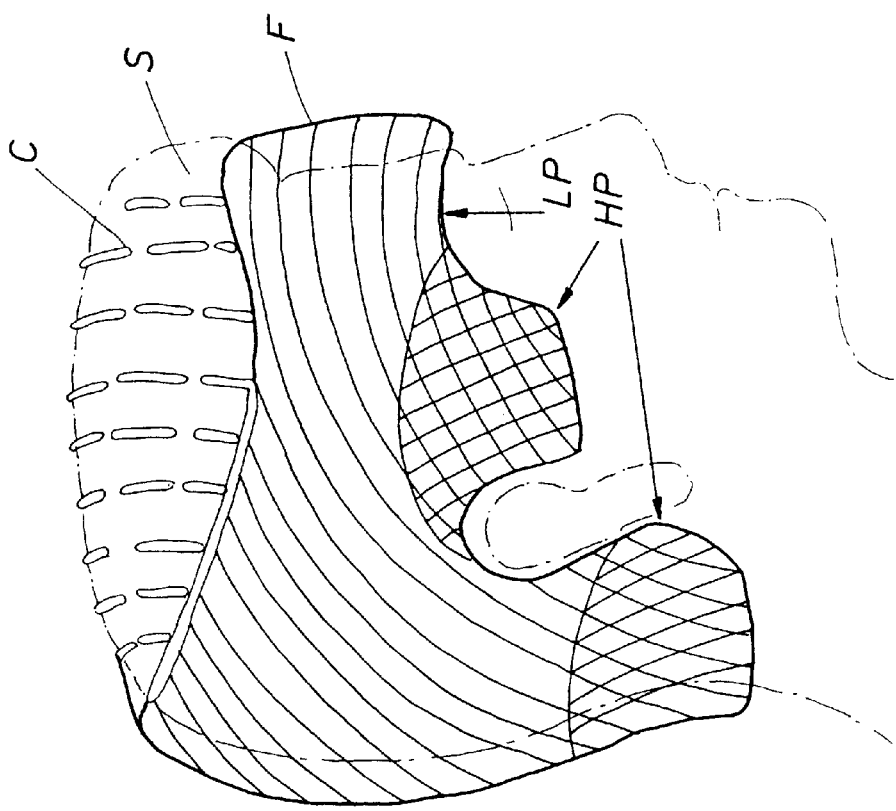

FIG. 10 shows a lateral view of skull surfaces exposed to ultrasound through probes enclosed upon a frame F. The lateral view illustrates high power HP areas for T-waves (the area anterior to the ear allows delivery of T-waves for the middle cerebral and terminal internal carotid arteries; the area posterior to the ear delivers T-waves for the basilar artery). The high power HP areas may also be used to deliver low power LP ultrasound between T-waves pulses since the same areas may help to create pressure gradients between affected and non-affected tissues (see selection of target tissues below).

Figure 11:
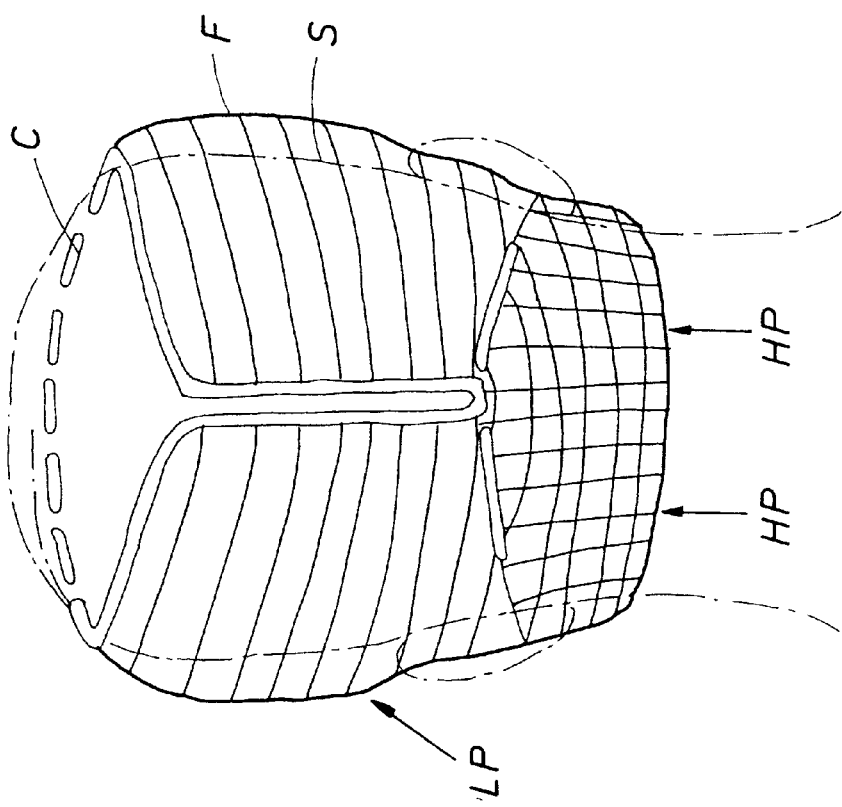

FIG. 11 shows a posterior view of skull surfaces exposed to ultrasound through probes enclosed upon a frame F. This view shows that low power LP areas cover almost all skull surface to achieve the exposure of maximum organ tissue to ultrasound. The posterior high power HP area covers entire access to foramen magnum to achieve maximum ultrasound transmission to terminal vertebral and basilar arteries (T-waves) and other waves to brainstem structures.

Figure 12:
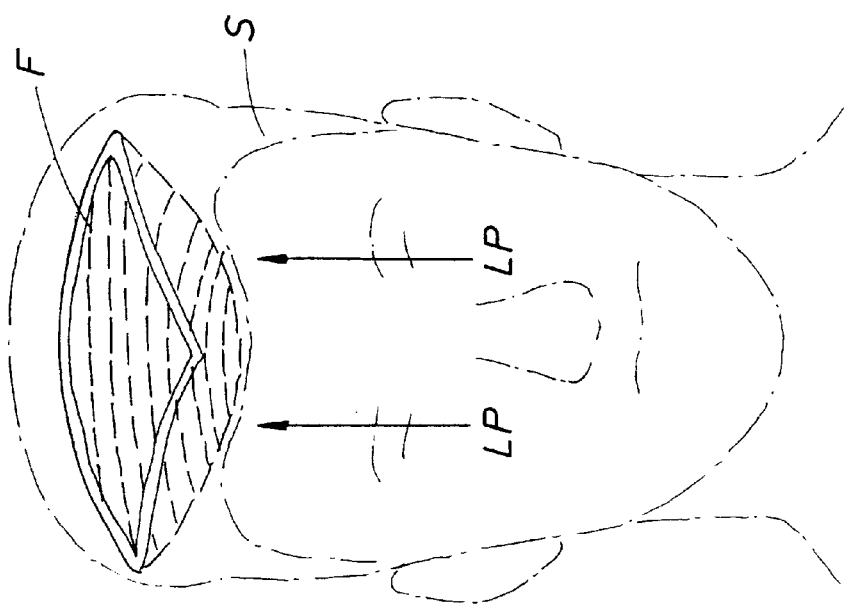

FIG. 12 shows an antero-posterior view of additional skull surfaces potentially exposed to ultrasound through probes attached to a frame F. This view shows an additional surface of the skull that can be exposed to ultrasound to transmit E, C, and P waves. This area can also be used to expose ischemic tissues in the anterior cerebral artery territory. This additional area can be used for P-waves to enhance pressure gradients towards the venous system. E, C, and P waves can be emitted from this additional area between cycles applied from other areas.

From the above FIGS. 9–12, it is illustrated how a frame may be constructed to be utilized in general with the apparatus and methodology of the present inventions. Frames may be organ specific. Frames in the manner of adjustable belts may be designed to be used with multiple organs.

Figure 13B:
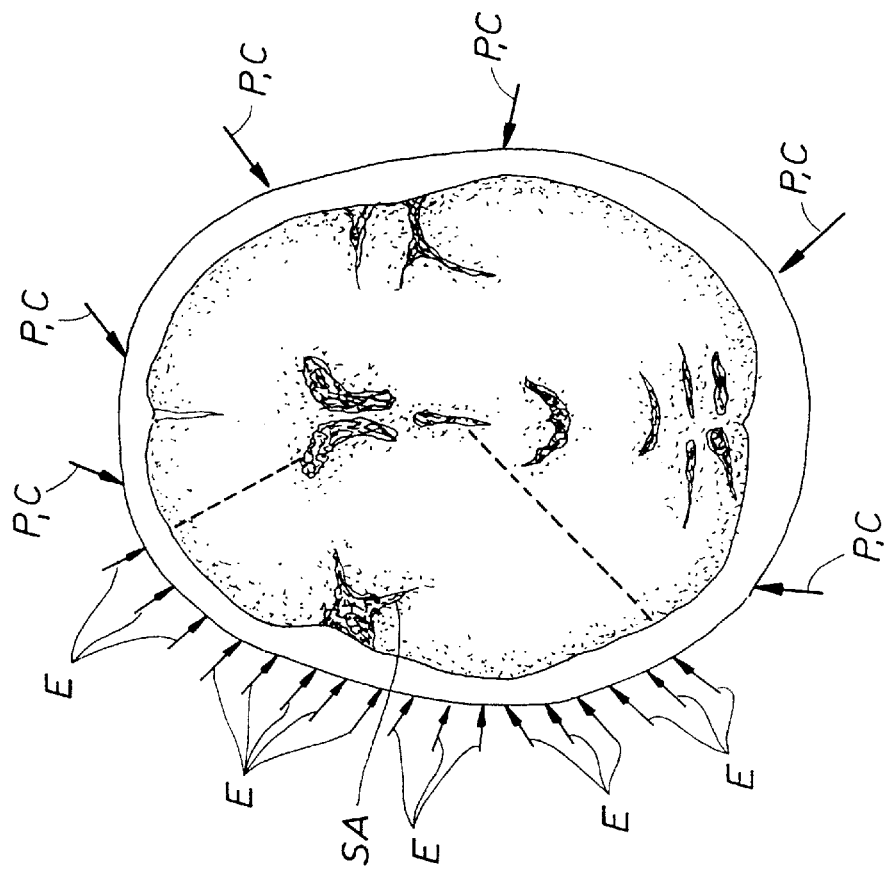
FIG. 13 represents findings in acute ischemic stroke in humans on brain computed tomography and illustrates how different brain tissues can be targeted using thrombolysis-enhancing, edema-reducing/energy delivering, and pressure-gradient creating waves to promote collateral flow and increase venous outflow.
Figure 13A:
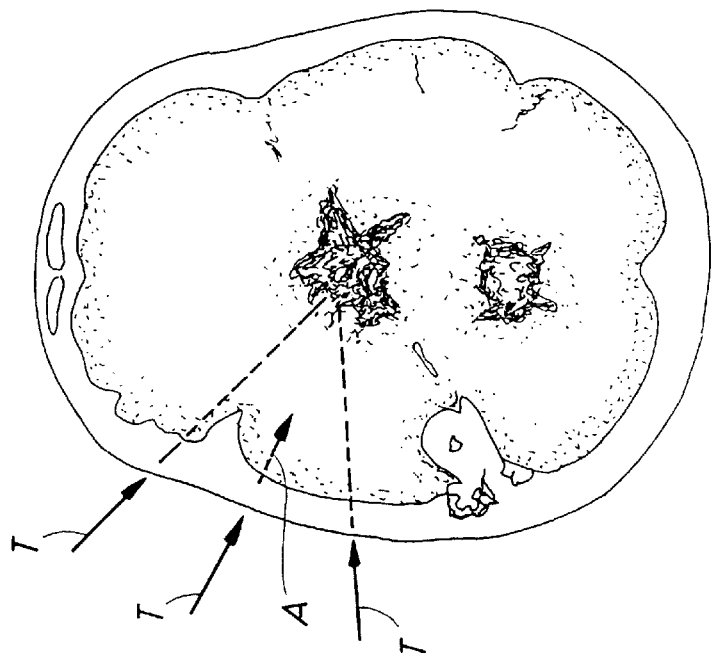

FIG. 13 shows a clinical neurological examination and imaging modalities, routinely employed, to evaluate stroke patients. Such can be used to identify target tissues, including organ tissue zone, ischemic tissue zone, normal donor tissue zones and zone boundaries, in accordance with the instant invention. FIG. 13 illustrates commonly found early ischemic changes on a non-contrast brain CT scan (transaxial planes) with a hyperdense middle cerebral artery (MCA) sign (left image, short dashed arrow A) and a loss of gray-white matter differentiation (right image, subcortical area SA between dotted lines).

In accordance with the instant invention, the ultrasound device of the instant invention would be targeted at the brain tissues of FIG. 13 by a clinician or technologist preferably, including selecting the areas of skull surface that will serve to deliver:

1. thrombolysis-enhancing waves (thick arrows, arrows T);
2. edema-reducing waves (E-waves, arrows E);

3. pressure gradient creating waves to promote collateral and interstitial flow (C-waves, arrows C); and 4. to increase venous outflow (P-waves, arrows P).

P-waves and C-waves cross boundaries Bd between identified normal tissue zones and ischemic tissue zones.

Figure 14:
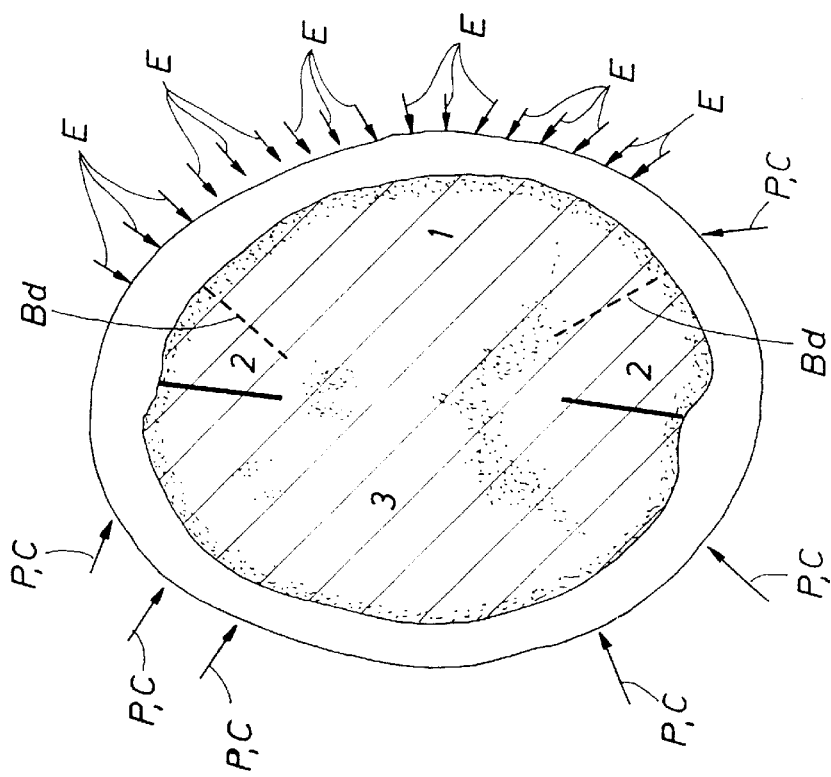
FIG. 14 shows arterial territory affected by ischemia in humans on a non-contrast head CT scan and its relationship to non-affected territories and how ultrasound waves can be directed through these territories, even beyond the window for thrombolysis.

Further in regard to the methods and apparatus of the instant invention, FIG. 14 shows exposure of an entire brain to ultrasound waves 1–3. FIG. 14 is aimed at the following: in patients with marked ischemic changes who are not eligible for thrombolysis with TPA, the apparatus can be used to:

1. to reduce edema in the territory 1, the left middle cerebral artery (MCA) territory with early ischemic tissue hypodensity;
2. to deliver energy, sonic and nutrients, to ischemic cells in the territory 1;
3. to propel or increase collateral and interstitial flow from the territories 2 to territory 1; and
4. to enhance pressure gradients between the territories 2 (border arterial territories of the anterior and posterior cerebral arterial of the unilateral hemisphere with normal tissue density) and 1, and to direct outflow towards the venous system.

In performing tasks 2–4, the beams are focused for crossing an identified boundary Bd between a normal tissue zone and an ischemic tissue zone.

Ultrasound waves are directed through:

1. unilateral skull towards territory 1 crossing it from cortex to deep matter and focusing on venous collectors;
2. uni- and contralateral skull towards territories 2 and crossing these territories towards adjacent territory 1 thereby focusing on watershed areas to promote collateral flow; and
3. contralateral skull towards territories 1 and 2 crossing territory 3 (contralateral hemisphere with normal tissue density) and focusing on areas with clots, edema and collateral flow to enhance pressure gradients that will enable streaming of fluids in the directions described above towards venous collectors.

FIG. 15 illustrates that clinical examination or other imaging modalities may show strokes of different severity and volumes of brain tissue involved. Clinical or imaging lesion localization can be used to target an ultrasound device in accordance with the present invention at one of the following lesion locations:

1. An entire arterial territory distal to its stem occlusion (i.e., middle, anterior, posterior cerebral arteries, basilar, vertebral arteries, or a combination thereof);
2. An arterial branch occlusion (any arterial territory);
3. Small vessel occlusive stroke (lacunar or deep white matter lesions in the anterior or posterior circulation);
4. Watershed territories between any arterial systems mentioned above; and/or
5. Posterior circulation strokes (arterial stem, branch, small vessel, or watershed localization.

An ultrasound device in accordance with the present invention can be targeted by an operator by selecting an anterior or posterior circulation approach and by applying various ultrasound waves to skull areas to enhance thrombolysis, reduce edema (arrows E), deliver energy (sonic or nutrients), deliver medications (lytics to clots and protectors to ischemic areas), and to promote collateral and interstitial flow (arrows P,C) to one or multiple selected areas.

Figure 16:
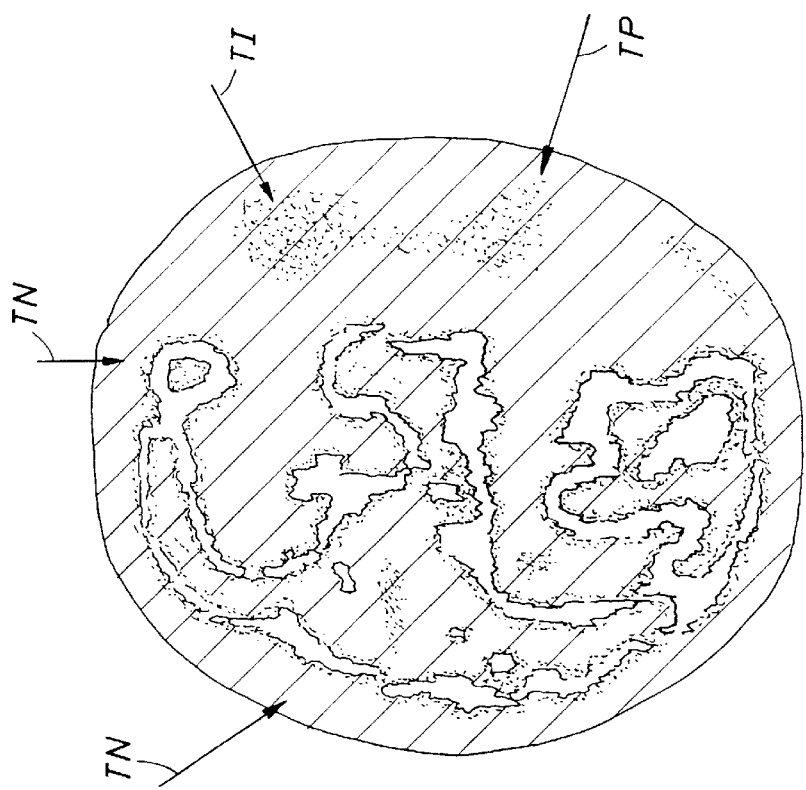
FIG. 16 illustrates findings on imaging modalities that show cerebral blood flow or related perfusion maps to identify tissues with severe ischemia, penumbra, and normal perfusion for tissue targeting with ultrasound.

FIG. 16 illustrates imaging modalities that can show cerebral blood flow (CBF), brain perfusion, and related metabolic parameters (oxygen extraction fraction, brain spectroscopy, etc.) Such techniques can be used to determine the tissue at risk and to direct application of ultrasound beams in accordance with the present invention. As discussed above, objectives of the direction of the ultrasound beams are:

1. Target tissue for direct energy transmission and nutrient delivery: tissue TI affected by most severe ischemia (CBF <8 ml/100 g/min);
2. Target penumbra tissues TP for maintenance of their function by means of edema reduction, energy, medication, and nutrient delivery and promotion of collateral flow, tissue that are maintaining some degree of flow on their own (penumbra or hypoperfused area with CBF 8–30 ml/100 g/min);
3. Target brain tissues TN with normal or <30 ml/100 g/min CBF which can be used as donor tissues for nutrient supply and as sources for enhancement of collateral and interstitial flow to hypoperfused areas.

Figure 17B:
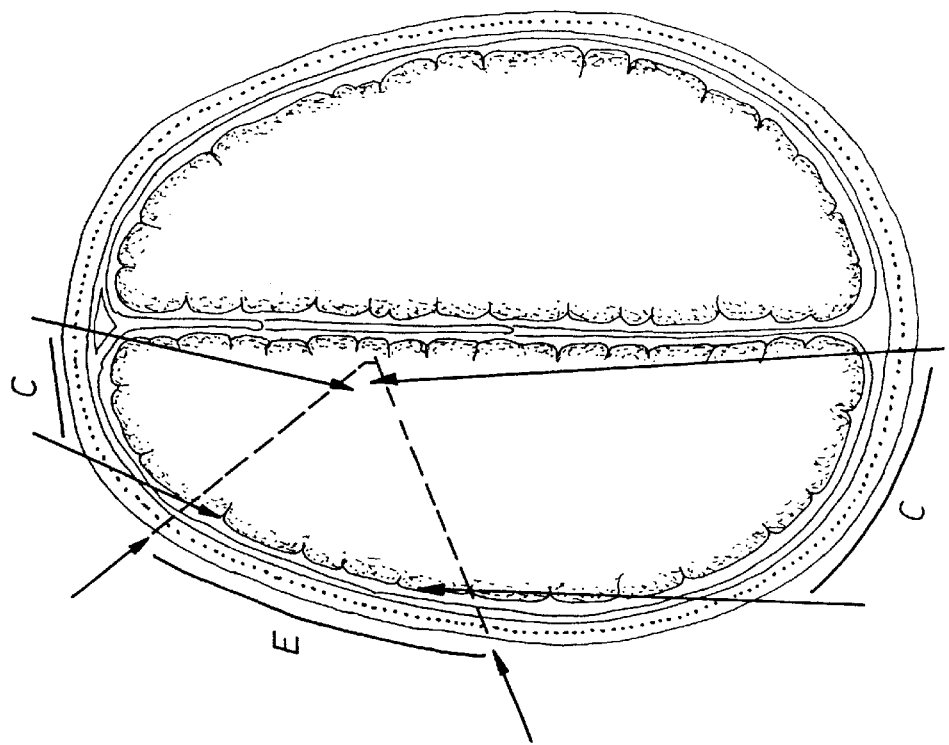
FIG. 17 shows a schematic drawing that illustrates ultrasound beam configuration.
Figure 17A:
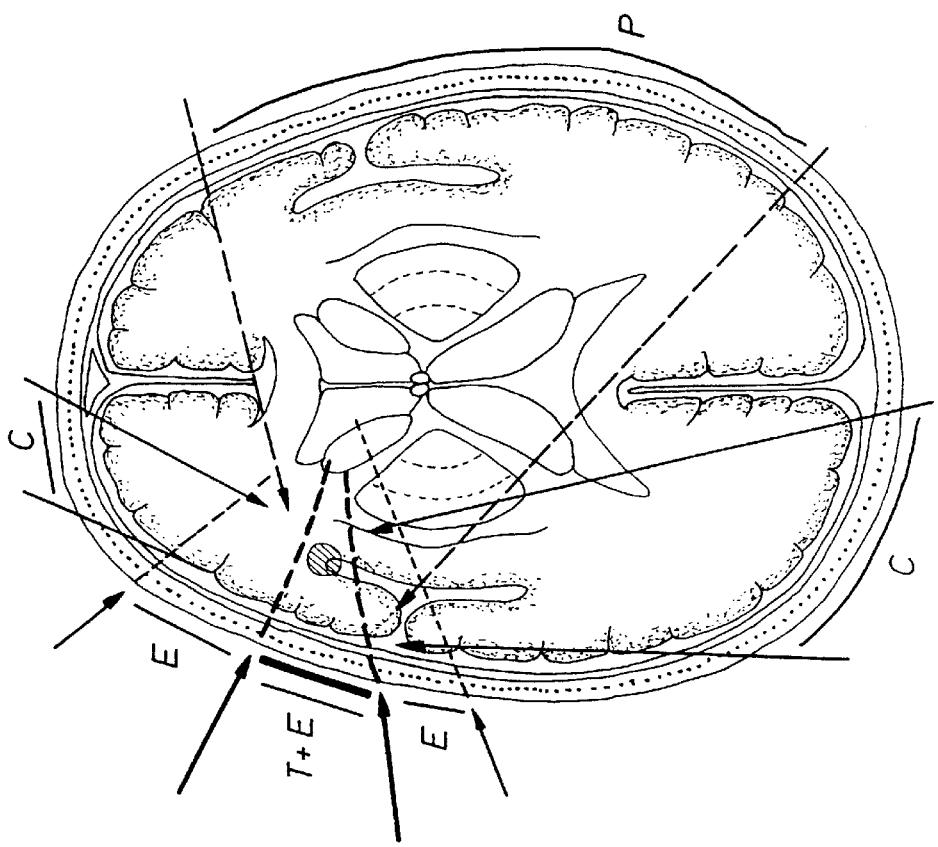

The ultrasound device can be targeted by an operator by selecting different beams that will target these tissues (see FIG. 17). FIG. 17 indicates an ultrasound device that will utilize single and/or multiple small (and/or large) surface emitting probes configured to transmit four types of beams (T beams, E beams, C beams and P beams) which may have different frequency, power and pulse configurations. Of course, one beam may perform the function of more than one type, e.g. E and T or C and P. The number of activated probes and the direction of beam propagation can be set by an operator when specific clot location and ischemic area are determined. Preferably, a level of automation can be utilized such that such information need only be entered into a device input block. Probe alignment and activation in accordance with the teachings of the invention can be effected by electronic steering or mechanically by hand help probe angulation followed by a firm fixation of selected position and/or activation, utilizing selected parts of headframe, for instance. According to one modality, all probes can initially emit test and/or diagnostic pulses at different frequency ranges (and/or power levels) to determine penetration through the bone by the strength of returned echoes and specific tissue response (i.e., Doppler shift for blood flow, power of the returned signals, etc.) Various types of returned echoes can be detected by the transducers and mechanical vibrations received are recoded back to electric pulses using piezo-electric effect and analyzed by the device. The best responding location, frequency, and pulse configuration can then be selected for continuing the emission of pulses arranged to achieve the following:

1. T-thrombolysis-enhancing beam
2. E-edema-reducing energy delivering beam
3. C-collateral and interstitial flow increasing beam
4. P-pressure gradient venous outflow enhancing beam Note: (•-indicates clot location in the Sylvian fissure.)

The diagram (right) of FIG. 17 also displays beams that can be activated when no significant penetration can be achieved if sound is scattered by falx structures at midline.

Figure 18:
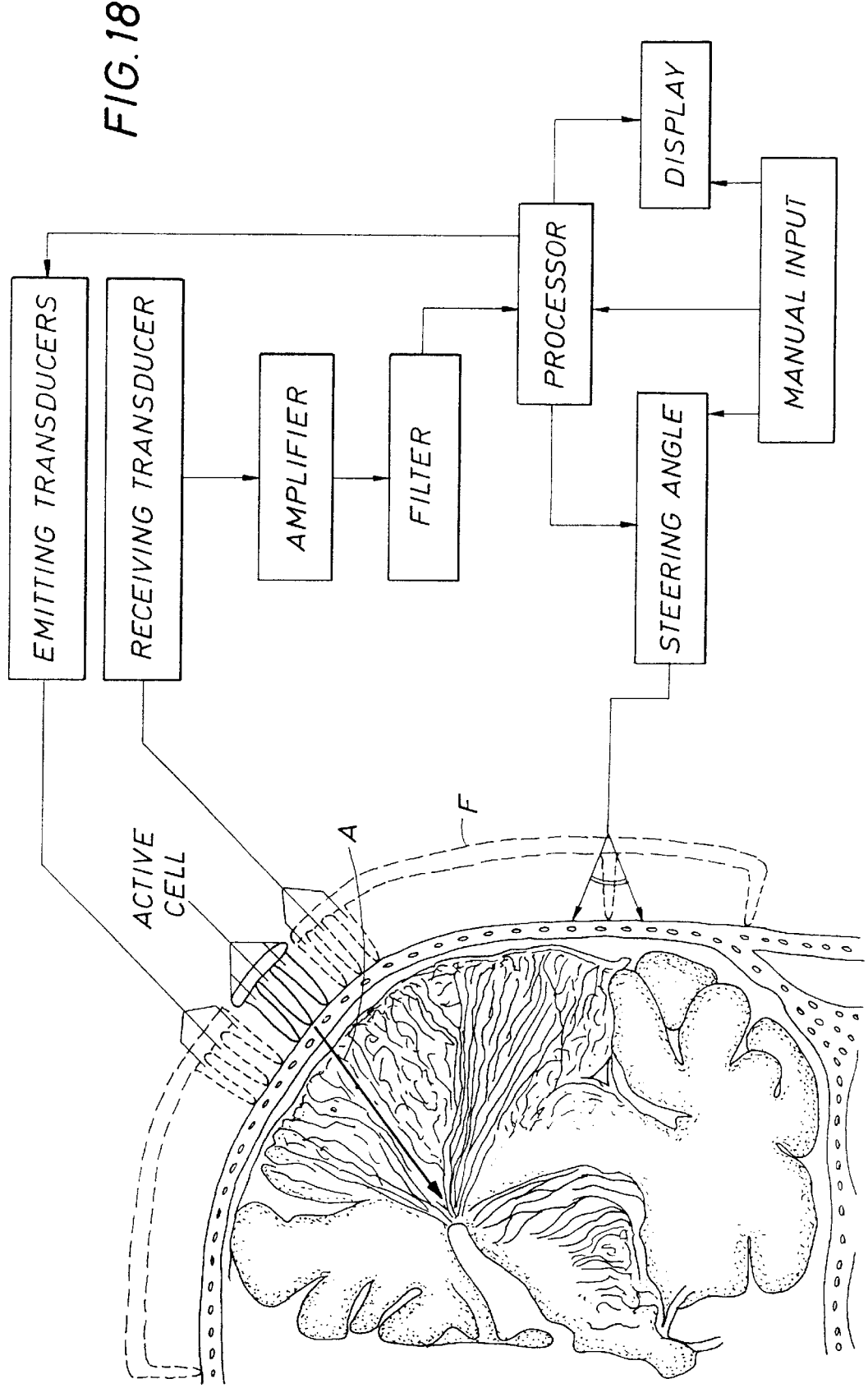
FIG. 18 represents a schematic drawing of transducer and device configuration in relationship to vascular anatomy and tissue targeting.

FIG. 18 illustrates how emitting probes may have effective surface that interacts with skin ranging from 1 $mm^2$ to an area equal or exceeding that of an entire target tissure or organ, i.e. clot, arterial bifurcation, arterial territory, lobe, hemisphere, etc. Receiving probes may have similar surface area range and may receive pulses from the area equal to one or multiple emitting probes.

Initially, according to one modality of the invention, the system would emit a set of pulses from all emitting probes (unless a specific area was pre-selected by manual input). Based on received signals, a processor can preferably determine which probes achieve best penetration and an electronic steering of the probes, in addition, can be performed to achieve maximum effects of ultrasound energy transmission under given penetrations at different bone regions.

The transducer configuration and signal processing are aimed to achieve the following:

1. Select optimal emitting surface area to transmit ultrasound waves through the bone or other surrounding tissues by avoiding excessive scattering in its porous structure (probe size, active cell number and/or beam width comparable to the inter-porous bone segments);
2. Steer the direction of ultrasound pulses along small arterial bed (coronal brain section with the direction of cortical and penetrating arterioles) to achieve maximum streaming of fluids (arrow A); and
3. Re-adjust setting if one of the therapeutic targets was achieved (T,E, C, P). For example, if the device detects returned signals consistent with complete arterial recanalization (as described in our clinical studies above), high power T-waves are discontinued. The device will switch to diagnostic monitoring of vessel patency instead of delivering therapeutic T-wave to minimize brain exposure to ultrasound energy.

Figure 19A:
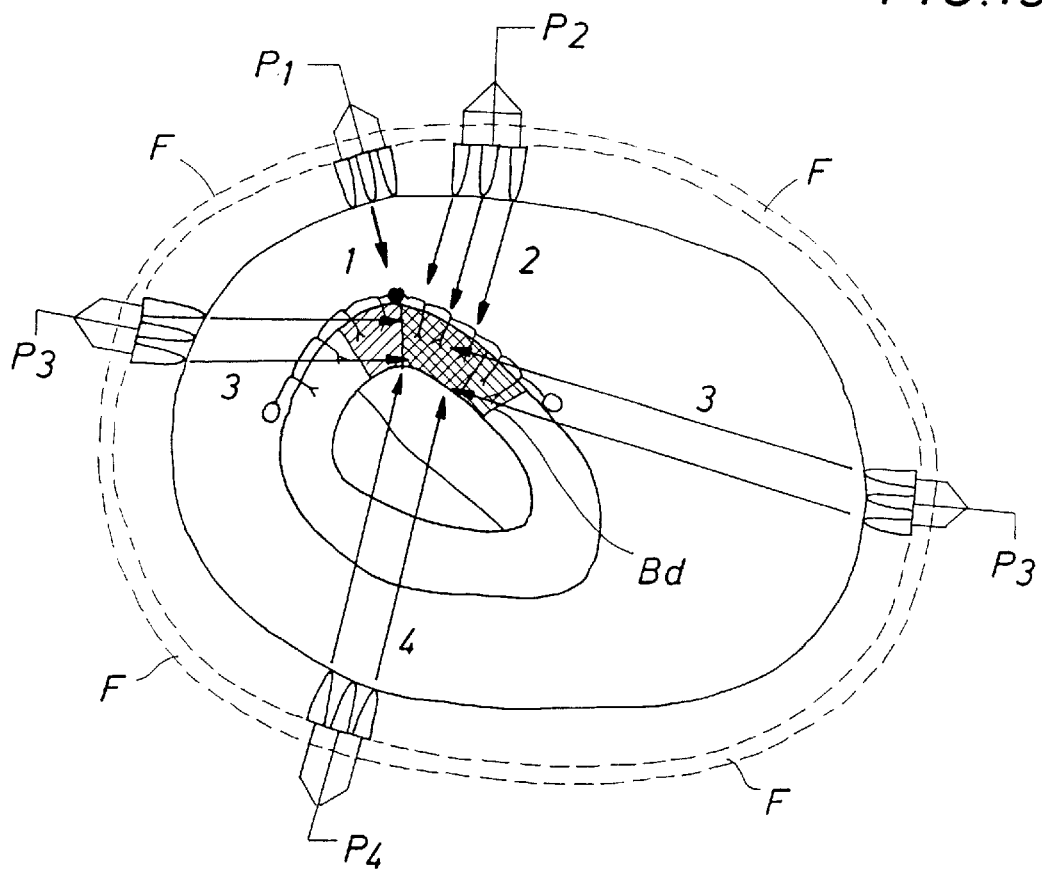
FIGS. 19A and 19B illustrate application of the apparatus and method to a heart organ.
Figure 19B:
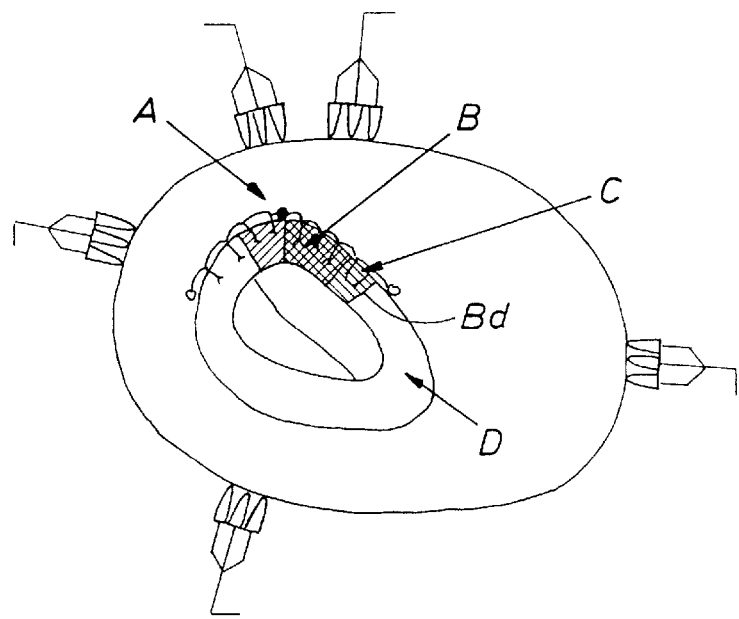

FIGS. 19 and 20 illustrate the application of the inventive methods and apparatus to organs other than the brain. FIGS. 19A and 19B relate to application of the apparatus and methods to a heart, as an example. Ultrasonic waves from probe P1 are designed to enhance thrombolysis aimed at clot location established from clinical-electrocardiographic examination or with other imaging modalities. Ultrasonic waves from probe P2 are focused to reduce edema (the device will assess returned echoes from myocardium and select optimal frequency, power and pulse-repetition frequency setting for E-waves since interstitial pressures in the heart muscle are different from the brain or other organs). Ultrasonic waves from probes P3 are directed to promote collateral and interstitial flow (these probes will be activated during heart muscle relaxation to increase promotion of end-diastolic flow to the ischemic part of the heart muscle: select probes can be used to image heart muscle contractions or a standard interface with electrocardiographic monitor can be used to identify diastolic phase of the cycle). Ultrasonic waves from probes located, structured and focused as probe P4 create pressure gradient towards venous collectors in diastoli. FIG. 19B illustrates the identification of an area A of thrombus, an area B of intense ischemia, areas C which qualify as border zones and areas D of normal tissue in a human organ using beams propagating at various degrees to each other through surrounding tissues.

Figure 20A:
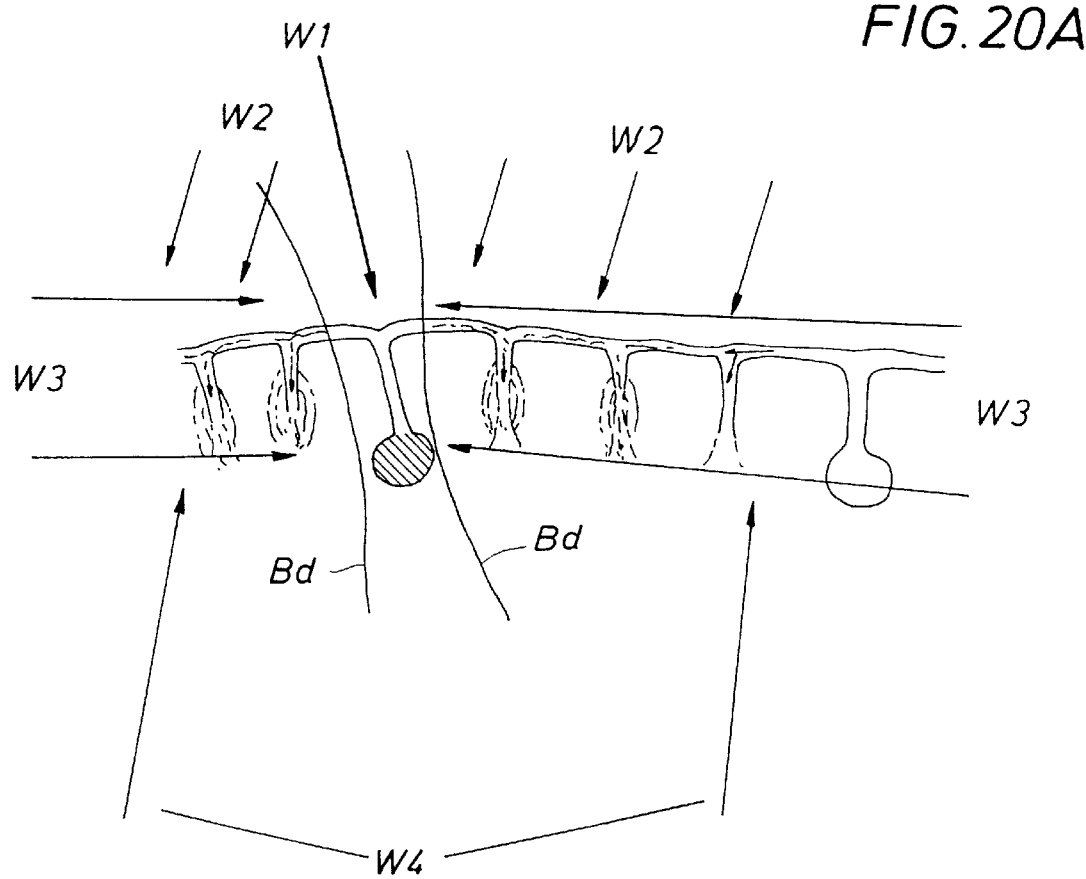
FIGS. 20A and 20B illustrate the arterial system of a parenchymatous organ and beam angulation and propagation.
Figure 20B:
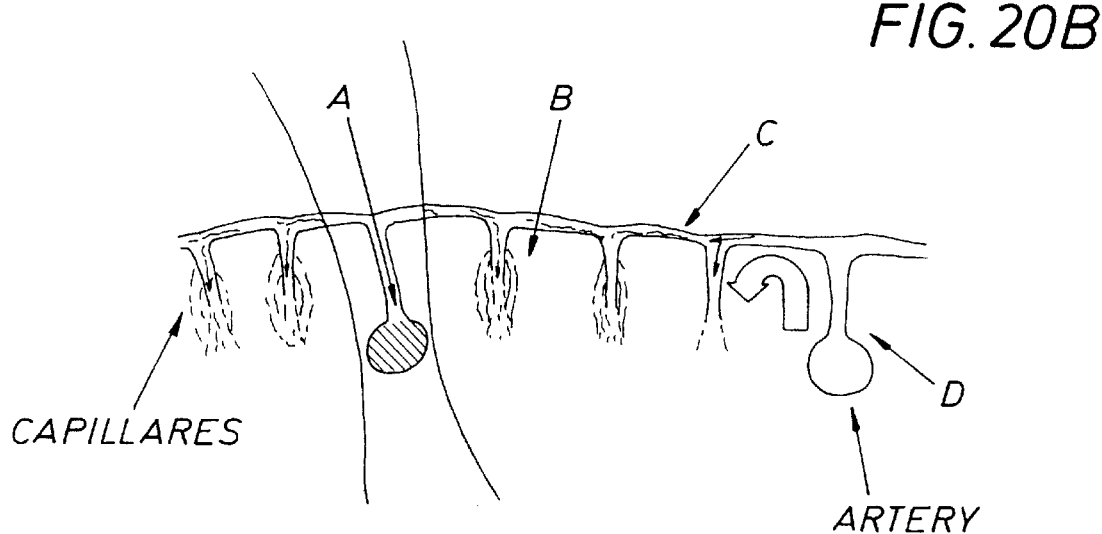

FIGS. 20A and 20B relate to an arterial system of a parenchymatous organ. FIGS. 20A and 20B illustrate beam angulation and propagation relating to the methods and apparatus of the instant invention. Ultrasonic waves W1 are directed for thrombolysis enhancing. Ultrasonic waves W2 are placed and directed for reducing edema. Ultrasonic waves W3 are located and focused to promote collateral flow. Ultrasonic waves W4 are situated to create pressure gradient towards venous outflow. In the parenchymatous organ, an area P of thrombolysis has been identified as well as area B of intense ischemia, area C of border zone and area D of normal tissue.

Again, when the claim language speaks of transmitted beams intersecting to define an included angle, that only makes literal sense if the beams literally define a common plane. It may be that the beams literally do not define a common plane, or precisely intersect. Thus, when two beams are spoken of as intersecting to define an included angle, it should be understood that if the beams do not literally intersect to define a common plane then one should measure the included angle from the projection of the beams onto the nearest common plane.

The foregoing disclosure and description of the invention are illustrative and explanatory thereof, and various changes in the size, shape, and materials, as well as in the details of the illustrated system may be made without departing from the spirit of the invention. The invention is claimed using terminology that depends upon a historic presumption that recitation of a single element covers one or more, and recitation of two elements covers two or more, and the like.

What is claimed is:

1. Apparatus for therapeutic insonation, comprising:
   an acoustic wave source structured for generating acoustic waves;
   a plurality of transducer probes attached to the acoustic wave source; and
   a frame structured to hold a plurality of probes, the frame of size and shape so as to at least partially surround an adult human organ and structured to orient the probes such that at least two probe transmitted beams intersect to define at least a 45° included angle; and wherein
   the acoustic wave source and transducer probes are structured in combination to produce a plurality of therapeutic beams wherein at least two probes produce beams of different (positive) power, including an essentially non-tissue destructive power level when applied for a period of at least several minutes.

2. Apparatus for therapeutic insonation, comprising:
   an acoustic wave source structured for generating acoustic waves;
   a plurality of transducer probes attached to the acoustic wave source; and
   a frame structured to hold a plurality of probes, the frame of size and shape so as to at least partially surround an adult human organ and structured to orient the probes such that at least two probe transmitted beams intersect to define at least a 45° included angle; and wherein
   the acoustic wave source and transducer probes are structured in combination to produce a plurality of therapeutic beams, with at least two beams having independently variable power levels, including an essentially non-tissue destructive power level when applied for a period of at least several minutes; and
   including a plurality of transducer probes attached to a receiver and input block to register returned signals and display relative diagnostic information.

3. The apparatus of claim 1 wherein the acoustic waves have
   a power between 1 mW and 1000 mW;
   a frequency between 1 kHz and 10,000 kHz; and
   a pulse rate of between 10/sec to continuous.

4. Apparatus for therapeutic insonation, comprising:
   an acoustic wave source structured for generating acoustic waves;
   a plurality of transducer probes attached to the acoustic wave source; and
   a frame structured to hold a plurality of probes, the frame of size and shape so as to at least partially surround an adult human organ and structured to orient the probes such that at least two probe transmitted beams intersect to define at least a 45° included angle; and wherein the generated acoustic waves have a power exceeding 1000 mW, producing waves of a power ranging between 1 mW and 1000 mW at target issue.

5. The apparatus of claim 1 wherein the probes each provide 1 mm² or more transmitting surface and provide in combination at least 25 cm² transmitting and/or receiving surface.

6. Apparatus for therapeutic insonation, comprising:
   an acoustic wave source structured for generating acoustic waves;
   a plurality of transducer probes attached to the acoustic wave source; and
   a frame structured to hold a plurality of probes, the frame of size and shape so as to at least partially surround an adult human organ and structured to orient the probes such that at least two probe transmitted beams intersect to define at least a 45° included angle; and
   wherein the frame comprises a belt.

7. The apparatus of claim 1 wherein the frame includes a circumferential structure that from partially to completely exposes target organ or tissue to probe beams.

8. The apparatus of claim 1 wherein the acoustic source is structured to fire acoustic beams from said probes sequentially.

9. The apparatus of claim 1 wherein the acoustic source is structured to fire acoustic beams from said probes simultaneously.

10. The apparatus of claim 1 wherein the acoustic source is structured to emit at least two beams of relatively narrow width, aimable so as to intersect in a predetermined area.

11. The apparatus of claim 10 wherein the acoustic source is structured to synchronize emissions from the said at least two beams to effect a positive beam re-enforcement for at least a portion of an area of intersection.

12. The apparatus of claim 1 wherein the acoustic source is structured to vary the power of at least one beam.

13. The apparatus of claim 1 wherein the acoustic source is structured to vary the frequency of at least one beam.

14. The apparatus of claim 1 wherein the acoustic source is structured to vary the pulse rate of at least one beam.

15. Apparatus for therapeutic-insonation, comprising:
   an acoustic wave source structured for generating acoustic waves;
   a plurality of transducer probes attached to the acoustic wave source; and
   a frame structured to hold a plurality of probes, the frame of size and shape so as to at least partially surround an adult human organ and structured to orient the probes such that at least two probe transmitted beams intersect to define at least a 45° included angle; and wherein
      the acoustic wave source and transducer probes are structured in combination to produce a plurality of therapeutic beams, with at least two beams having independently variable power levels, including an essentially non-tissue destructive power level when applied for a period of at least several minutes; and
      wherein the acoustic source is structured to receive a transmitted wave for diagnostic purposes with at least one probe.

16. The apparatus of claim 1 wherein the frame is structured to hold a plurality of probes arranged to at least partially surround a human organ such that at least two probe transmitting beams intersect to define at least a 90° included angle.

17. The apparatus of claim 1 wherein the frame is structured to hold a plurality of probes arranged to at least partially surround a human organ such that at least two transmitting beams intersect to define at least a 135° included angle.

18. The apparatus of claim 1 wherein the frame is structured in combination with the probes to hold a plurality of probes arranged to at least partially surround a human organ such that a plurality of transmitting beams intersect to define a relatively continuous included angle of at least 45°.

19. The apparatus of claim 1 wherein the acoustic source includes at least one of mechanical and electronic steering for aligning and activating probes.

20. A method for the therapeutic use of ultrasound to enhance perfusion of tissue, comprising:
   identifying, in at least one organ tissue zone, a boundary between at least one normal tissue zone and at least one ischemic tissue zone;
   arranging a plurality of probes to direct acoustic beams into the organ tissue zone, the beams focused to span an angle of at least 45°, with at least one beam passing through the boundary to induce fluid motion across the boundary;
   applying insonation through the probes to the organ tissue zone for at least a minute;
   acoustically monitoring, at least periodically, indicia of perfusion for at least a portion of the organ tissue zone; and
   producing a plurality of therapeutic beams with independently variable power levels, including essentially non-tissue destructive power levels over periods of transmission of at least several minutes.

21. A method for the therapeutic use of ultrasound to enhance perfusion of tissue, comprising:
   identifying, in at least one organ tissue zone, a boundary between at least one normal tissue zone and at least one ischemic tissue zone;
   arranging a plurality of probes to direct acoustic beams into the organ tissue zone, the beams focused to span an angle of at least 45°, with at least one beam passing through the boundary to induce fluid motion across the boundary;
   applying insonation through the probes to the organ tissue zone for at least a minute;
   acoustically monitoring, at least periodically, indicia of perfusion for at least a portion of the organ tissue zone; and
   applying insonation for up to 24 hours.

22. The method of claims 20 or 21 including applying repeated sonication of variable duration.

23. The method of claims 20 or 21 that includes applying at least one beam along an arterial structure towards a tissue zone with flow obstruction.

24. The method of claims 20 or 21 that includes applying at least two beams towards the ischemic tissue zone such that at least two beams span an included angle of at least 45.

25. The method of claims 20 or 21 that includes applying a plurality of beams toward the ischemic tissue zone from directions such that the beams relatively continuously span an at least 45 included angle.

26. The method of claims 20 or 21 that includes identifying a target zone and locating and focusing beams and emitting waves timed such that peaks from at least two waves coincide at the target zone.

27. The method of claims 20 or 21 that includes identifying a target zone and locating and focusing beams and emitting waves times such that peaks and troughs from at least two waves coincide, the waves spanning between them at least a 90 angle.

28. A method for the therapeutic use of ultrasound to enhance perfusion of tissue, comprising:
   identifying, in at least one organ tissue zone, a boundary between at least one normal tissue zone and at least one ischemic tissue zone;
   arranging a plurality of probes to direct acoustic beams into the organ tissue zone, the beams focused to span an angle of at least 45°, with at least one beam passing through the boundary to induce fluid motion across the boundary;
   applying insonation through the probes to the organ tissue zone for at least a minute;
   acoustically monitoring, at least periodically, indicia of perfusion for at least a portion of the organ tissue zone; and
   testing an indicia of effectiveness of a beam for an arranged and focused probe and selecting probes to be utilized based upon the testing.

29. The method of claims 20 or 21 that includes aligning and activating probes with at least one of mechanical and electronic steering.

30. The method of claims 20 or 21 that includes emitting test pulse beams at different frequency ranges from arranged and focused probes and estimating penetration through bone by an indicia of strength of returned echoes.

31. The method of claims 20 or 21 that includes selecting a position and focus for at least one beam based upon bone or other surrounding tissue structure around the at least one organ tissue zone.

32. The method of claims 20 or 21 that includes selecting a position and focus for at least one beam based upon bone or other surrounding tissue structure around the at least one organ tissue zone.

33. The method of claims 20 or 21 including firing acoustic beams from the probes sequentially.

34. A method for the therapeutic use of ultrasound to enhance perfusion of tissue, comprising:
   identifying, in at least one organ tissue zone, a boundary between at least one normal tissue zone and at least one ischemic tissue zone;
   arranging a plurality of probes to direct acoustic beams into the organ tissue zone, the beams focused to span an angle of at least 45°, with at least one beam passing through the boundary to induce fluid motion across the boundary;
   applying insonation through the probes to the organ tissue zone for at least a minute;
   acoustically monitoring, at least periodically, indicia of perfusion for at least a portion of the organ tissue zone; and
   emitting at least two beams of relatively narrow focus and steering the beams to intersect.

35. The method of claims 20 or 21 that includes synchronizing emissions from at least two beams to effect positive beam reinforcement at least at a portion of an area of intersection.

36. The method of claims 20 or 21 including producing a plurality of beams of varying power within a range of from 1 mW to 1000 mW.

37. A method for the therapeutic use of ultrasound to enhance perfusion of tissue, comprising:
   identifying, in at least one organ tissue zone, a boundary between at least one normal tissue zone and at least one ischemic tissue zone;
   arranging a plurality of probes to direct acoustic beams into the organ tissue zone, the beams focused to span an angle of at least 45°, with at least one beam passing through the boundary to induce fluid motion across the boundary;
   applying insonation through the probes to the organ tissue zone for at least a minute;
   acoustically monitoring, at least periodically, indicia of perfusion for at least a portion of the organ tissue zone; and
   externally applying beams to achieve beams of power within a range of 1 mW to 1000 mW at target tissues.

38. A method for the therapeutic use of ultrasound to enhance perfusion of tissue, comprising:
   identifying, in at least one organ tissue zone, a boundary between at least one normal tissue zone and at least one ischemic tissue zone;
   arranging a plurality of probes to direct acoustic beams into the organ tissue zone, the beams focused to span an angle of at least 45°, with at least one beam passing through the boundary to induce fluid motion across the boundary;
   applying insonation through the probes to the organ tissue zone for at least a minute;
   acoustically monitoring, at least periodically, indicia of perfusion for at least a portion of the organ tissue zone; and
   varying the frequency of a plurality of beams within a range of from 1 KHz to 10 Mhz and varying the pulse rate of a plurality of beams within a range of from 10/second to continuous.

39. The method of claim 20 including producing a plurality of beams with independently variable power levels where power varies either intermittently or sequentially or both.

40. A method for the therapeutic use of ultrasound to enhance perfusion of tissue, comprising:
   identifying, in at least one organ tissue zone, a boundary between at least one normal tissue zone and at least one ischemic tissue zone;
   arranging a plurality of probes to direct acoustic beams into the organ tissue zone, the beams focused to span an angle of at least 45°, with at least one beam passing through the boundary to induce fluid motion across the boundary;
   applying insonation through the probes to the organ tissue zone for at least a minute;
   acoustically monitoring, at least periodically, indicia of perfusion for at least a portion of the organ tissue zone; and
   producing a plurality of beams with independently variable frequency.

41. A method for the therapeutic use of ultrasound to enhance perfusion of tissue, comprising:
   identifying, in at least one organ tissue zone, a boundary between at least one normal tissue zone and at least one ischemic tissue zone;
   arranging a plurality of probes to direct acoustic beams into the organ tissue zone, the beams focused to span an angle of at least 45°, with at least one beam passing through the boundary to induce fluid motion across the boundary;
   applying insonation through the probes to the organ tissue zone for at least a minute;

acoustically monitoring, at least periodically, indicia of perfusion for at least a portion of the organ tissue zone; and producing a plurality of beams with independently variable pulse rate.

42. The method of claim 20 that includes applying insonation to promote the effect of thrombolysis.

43. A method for the therapeutic use of ultrasound to enhance perfusion of tissue, comprising:

identifying, in at least one organ tissue zone, a boundary between at least one normal tissue zone and at least one ischemic tissue zone;

arranging a plurality of probes to direct acoustic beams into the organ tissue zone, the beams focused to span an angle of at least 45°, with at least one beam passing through the boundary to induce fluid motion across the boundary;

applying insonation through the probes to the organ tissue zone for at least a minute;

acoustically monitoring, at least periodically, indicia of perfusion for at least a portion of the organ tissue zone; and applying insonation to promote the effect of tissue protective therapy.

44. A method for the therapeutic use of ultrasound to enhance perfusion of tissue, comprising:

identifying, in at least one organ tissue zone, a boundary between at least one normal tissue zone and at least one ischemic tissue zone;

arranging a plurality of probes to direct acoustic beams into the organ tissue zone, the beams focused to span an angle of at least 45°, with at least one beam passing through the boundary to induce fluid motion across the boundary;

applying insonation through the probes to the organ tissue zone for at least a minute;

acoustically monitoring, at least periodically, indicia of perfusion for at least a portion of the organ tissue zone; and applying insonation to deliver nutrients to ischemic tissue.

45. The method of claims 20 or 21 that includes applying insonation to enhance ischemic tissue vitality microcirculation and perfusion until normal blood flow is restored.

46. Apparatus for therapeutic insonation, comprising:

an acoustic wave source structured for generating acoustic waves;

a plurality of transducer probes attached to the acoustic wave source;

a frame structured to hold a plurality of probes, the frame of size and shape so as to at least partially surround an adult human organ and structured to orient the probes such that at least two probe transmitted beams intersect to define at least a 45° included angle; and a source of cardiac pulsation information and wherein the acoustic wave emits waves of frequency and pulse repetition in synchronization with the cardiac pulsation information.

47. Apparatus for therapeutic insonation, comprising:

an acoustic wave source structured for generating acoustic waves;

a plurality of transducer probes attached to the acoustic wave source;

a frame structured to hold a plurality of probes, the frame of size and shape so as to at least partially surround an adult human organ and structured to orient the probes such that at least two probe transmitted beams intersect to define at least a 45° included angle; and a source of systemic hemo-dynamic information and wherein the acoustic wave source emits waves of frequency and wave pulse repetition in synchronization with the hemo-dynamic information.

48. A method for the therapeutic use of ultrasound to enhance perfusion of tissue, comprising:

identifying, in at least one organ tissue zone, a boundary between at least one normal tissue zone and at least one ischemic tissue zone;

arranging a plurality of probes to direct acoustic beams into the organ tissue zone, the beams focused to span an angle of at least 45°, with at least one beam passing through the boundary to induce fluid motion across the boundary;

applying insonation through the probes to the organ tissue zone for at least a minute;

acoustically monitoring, at least periodically, indicia of perfusion for at least a portion of the organ tissue zone; and securing cardiac pulsation information and synchronizing an acoustic wave frequency and pulse repetition with the cardiac pulsation information.

49. A method for the therapeutic use of ultrasound to enhance perfusion of tissue, comprising:

identifying, in at least one organ tissue zone, a boundary between at least one normal tissue zone and at least one ischemic tissue zone;

arranging a plurality of probes to direct acoustic beams into the organ tissue zone, the beams focused to span an angle of at least 45°, with at least one beam passing through the boundary to induce fluid motion across the boundary;

applying insonation through the probes to the organ tissue zone for at least a minute;

acoustically monitoring, at least periodically, indicia of perfusion for at least a portion of the organ tissue zone; and securing systemic hemo-dynamic information and synchronizing an acoustic wave frequency and pulse repetition with the hemo-dynamic information.

50. The method of claims 48 or 49 that includes applying information to promote the effect of ultrasound enhanced natural thrombolysis.

51. The apparatus of claim 1 wherein the acoustic wave source and transducer probes are structured in combination to produce a plurality of therapeutic beams with independently variable power levels and such that two power levels can be produced intermittently on one beam.

52. The apparatus of claim 1 wherein the acoustic wave source and transducer probes are structured in combination to produce a plurality of therapeutic beams with independently variable power levels and such that two power levels can be produced simultaneously on two different beams.

* * * * *